US010893803B2

(12) United States Patent
Massie et al.

(10) Patent No.: US 10,893,803 B2
(45) Date of Patent: *Jan. 19, 2021

(54) WIDE-FIELD RETINAL IMAGING SYSTEM

(71) Applicant: Phoenix Technology Group LLC, Pleasanton, CA (US)

(72) Inventors: Norbert A. Massie, Pleasanton, CA (US); Stephan Hoffmann, Pleasanton, CA (US); Jack Schmidt, Woodinville, WA (US); Ned Nestorovic, Woodinville, WA (US)

(73) Assignee: PHOENIX TECHNOLOGY GROUP LLC, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/271,645

(22) Filed: Feb. 8, 2019

(65) Prior Publication Data

US 2019/0239744 A1  Aug. 8, 2019

Related U.S. Application Data

(63) Continuation of application No. 15/860,346, filed on Jan. 2, 2018, now Pat. No. 10,244,943, which is a (Continued)

(51) Int. Cl.
*A61B 3/14* (2006.01)
*A61B 3/10* (2006.01)
(Continued)

(52) U.S. Cl.
CPC ............ *A61B 3/158* (2013.01); *A61B 3/0025* (2013.01); *A61B 3/102* (2013.01); *A61B 3/125* (2013.01);
(Continued)

(58) Field of Classification Search
CPC .. A61B 3/156; A61B 3/14; A61B 3/12; A61B 3/158; A61B 3/0025
(Continued)

(56) References Cited

U.S. PATENT DOCUMENTS 5,608,472 A   3/1997   Szirth et al.
5,751,395 A   5/1998   Thall et al.
(Continued)

FOREIGN PATENT DOCUMENTS

EP   3127475     2/2017
JP   5875533 A   5/1983
(Continued)

OTHER PUBLICATIONS

EP16183029.4, "Extended European Search Report", dated Mar. 30, 2017, 13 pages.
(Continued)

*Primary Examiner* — Mohammed A Hasan
(74) *Attorney, Agent, or Firm* — Kilpatrick Townsend & Stockton LLP

(57) ABSTRACT

A retinal imager for imaging a retina of an eye includes an illumination source operable to generate illumination light and a beam splitter operable to receive the illumination light and direct the illumination light along an optical axis. The retinal imager also includes a field lens disposed along the optical axis and an objective lens disposed along the optical axis and operable to contact a cornea of the eye. An aerial image is formed adjacent to the field lens. The retinal imager further includes an image sensor and one or more lenses disposed along the optical axis between the beam splitter and the image sensor. The one or more lenses are operable to form a sensor image at the image sensor.

20 Claims, 46 Drawing Sheets

Related U.S. Application Data continuation of application No. 15/228,669, filed on Aug. 4, 2016, now Pat. No. 9,872,618.

(60) Provisional application No. 62/201,243, filed on Aug. 5, 2015.

(51) Int. Cl.
*A61B 3/00* (2006.01)
*A61B 3/15* (2006.01)
*A61B 3/12* (2006.01)
*A61B 3/125* (2006.01)
*G02B 27/00* (2006.01)

(52) U.S. Cl.
CPC ........ *A61B 3/1208* (2013.01); *G02B 27/0018* (2013.01)

(58) Field of Classification Search
USPC ........................................ 351/207
See application file for complete search history.

(56) References Cited

U.S. PATENT DOCUMENTS

| | | |
|---|---|---|
| 5,822,036 A | 10/1998 | Massie et al. |
| 9,872,618 B2 | 1/2018 | Massie et al. |
| 10,244,943 B2 * | 4/2019 | Massie ............... A61B 3/102 |
| 2003/0103063 A1 * | 6/2003 | Mojaver ............. G06T 3/00 345/647 |
| 2007/0263171 A1 * | 11/2007 | Ferguson ............ A61B 3/102 351/206 |
| 2008/0309876 A1 * | 12/2008 | Massie ............... A61B 3/12 351/219 |
| 2012/0184857 A1 | 7/2012 | Yokosuka et al. |
| 2012/0287255 A1 | 11/2012 | Ignatovich et al. |
| 2014/0267668 A1 | 9/2014 | Marcus et al. |
| 2015/0173613 A1 | 6/2015 | Gerrans et al. |
| 2017/0035294 A1 | 2/2017 | Massie et al. |

FOREIGN PATENT DOCUMENTS

| | | |
|---|---|---|
| JP | 2005168941 A | 6/2005 |
| JP | 2016518889 A | 6/2016 |
| WO | 2010034502 A2 | 4/2010 |

OTHER PUBLICATIONS

ISO 10940:2009, Retrieved from the Internet: URL:http://www.iso.orgjisojhomejstorejcataloguetcjcataloguedetail.htm?csnumber=39140, Aug. 1, 2009.
JP2016-153878, "Office Action", dated Aug. 21, 2020, 11 pages.

* cited by examiner

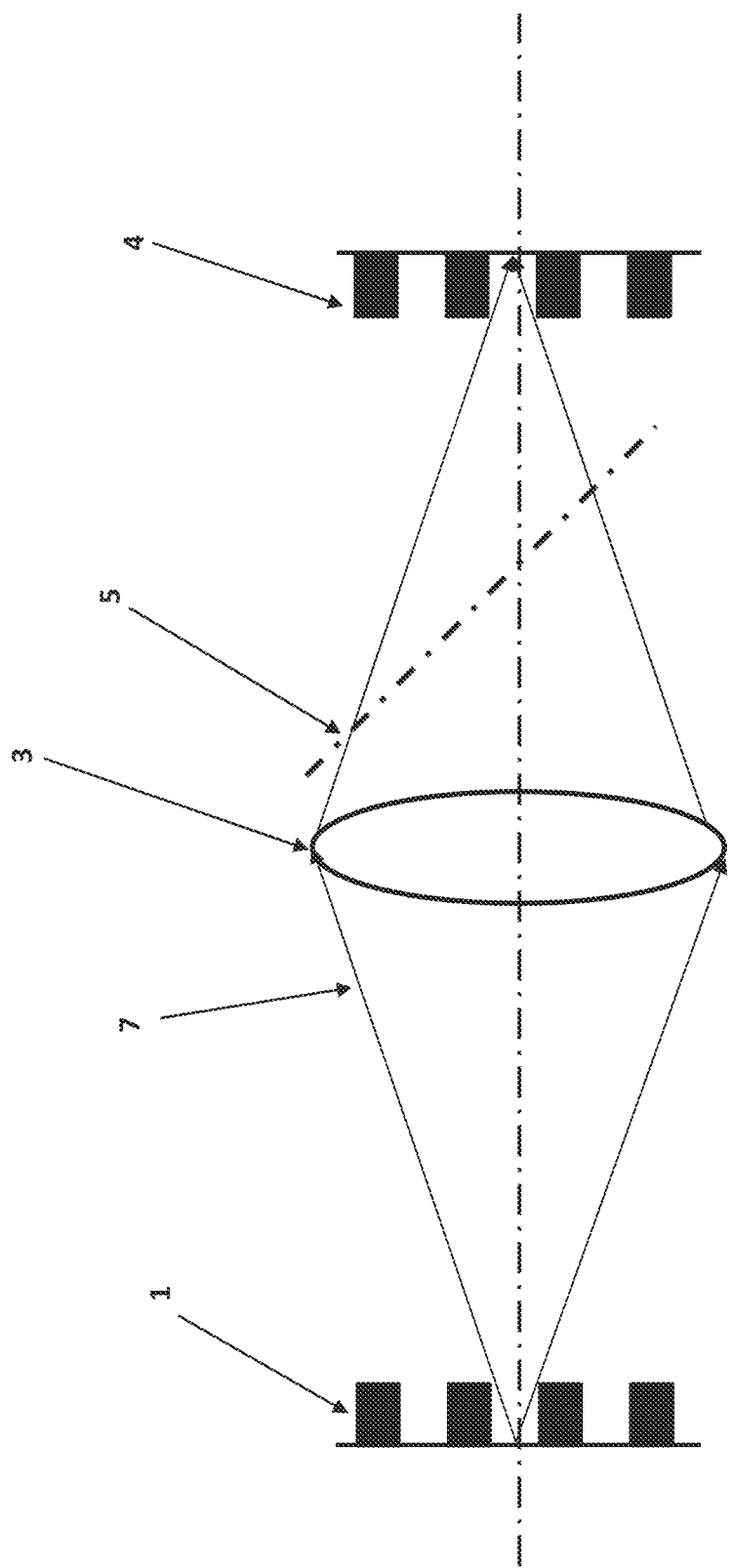

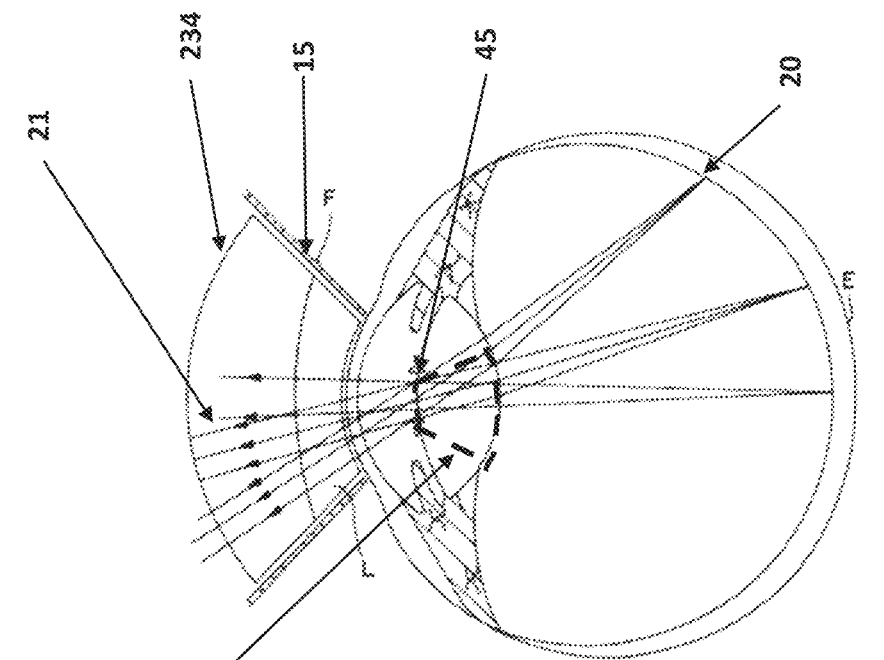
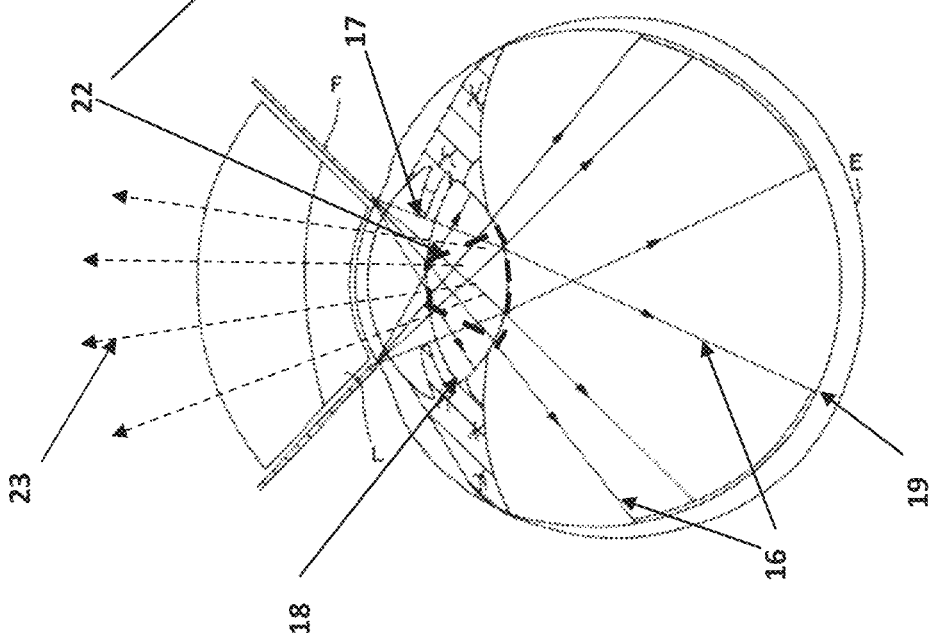
Figure 2A (Prior Art)
Figure 2B (Prior Art)

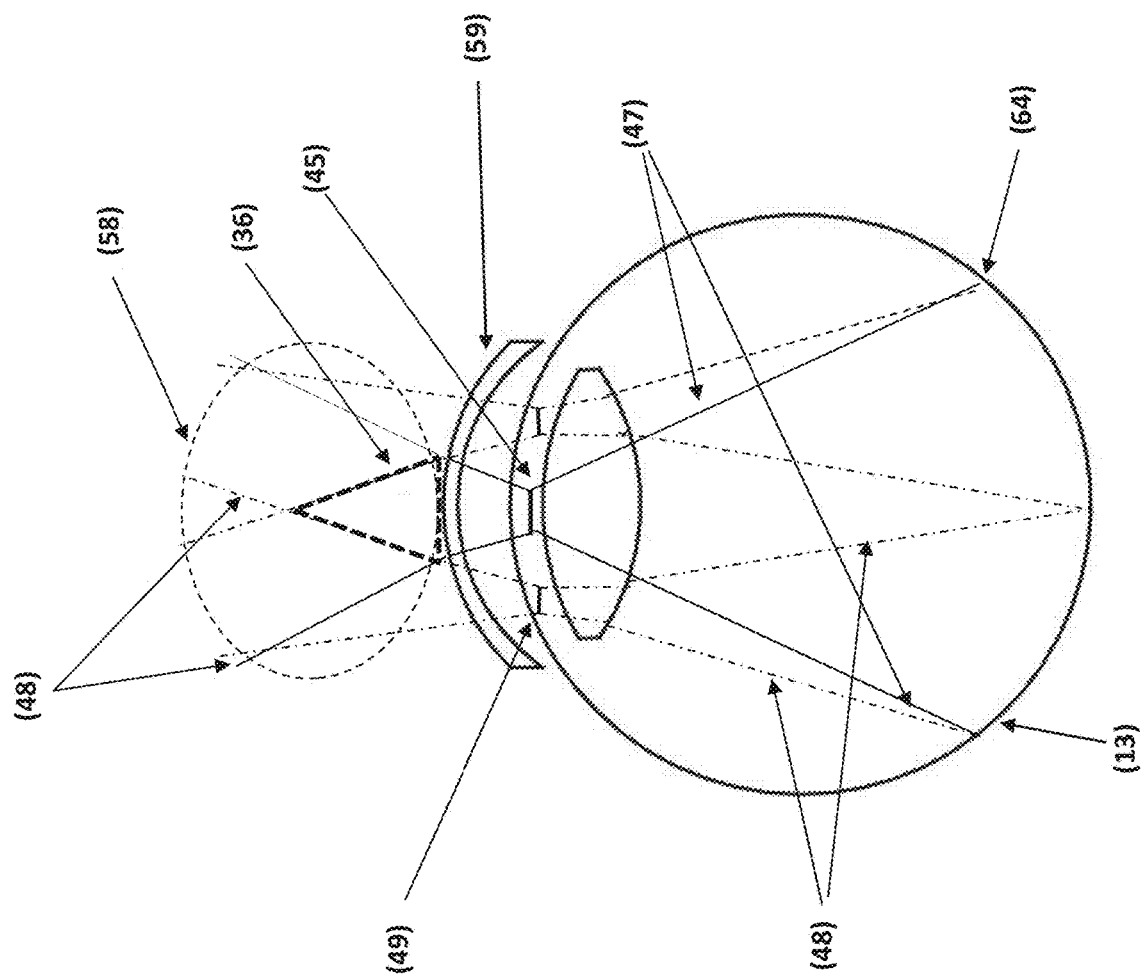

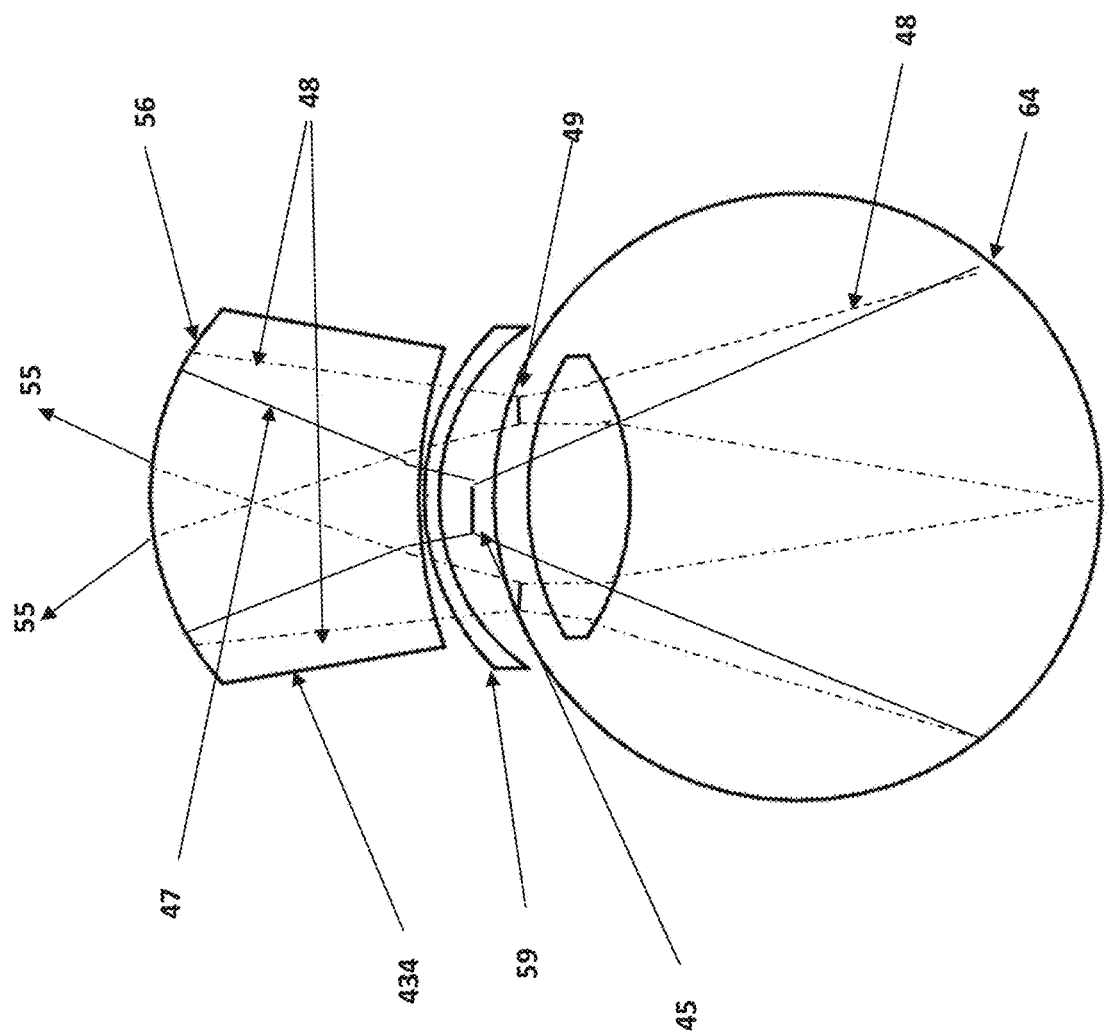

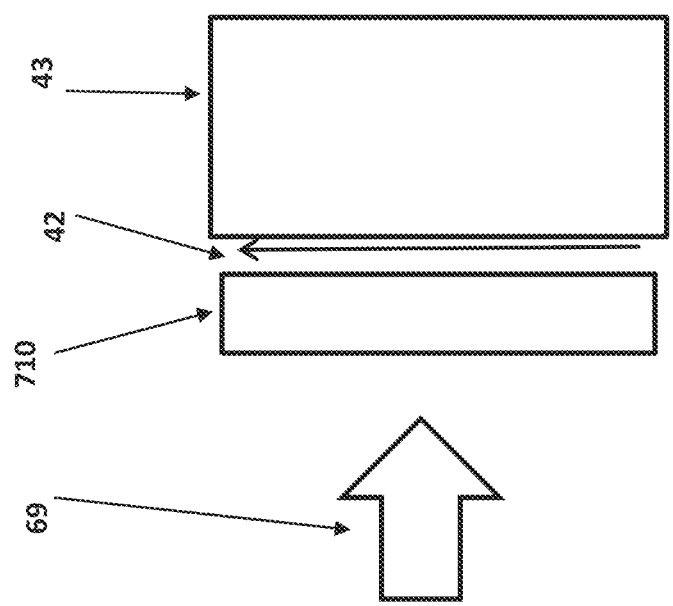

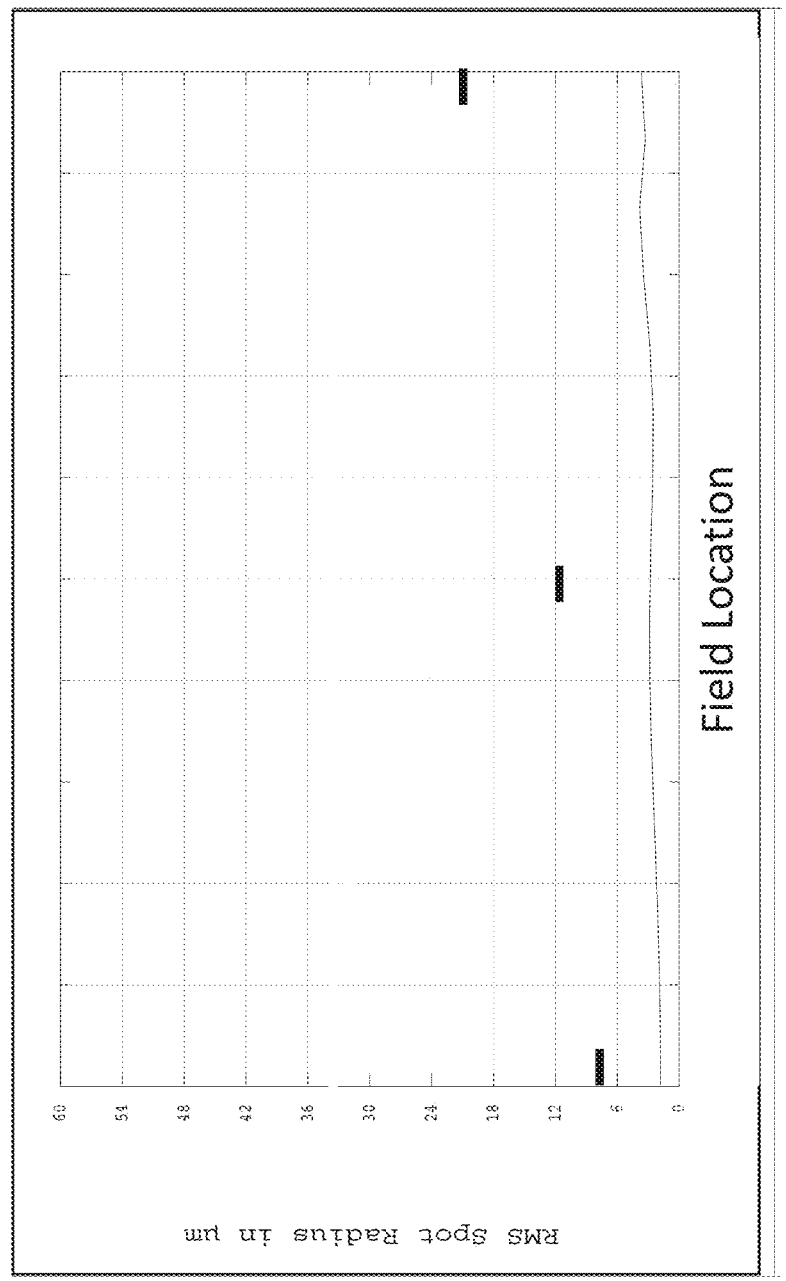

WIDE-FIELD RETINAL IMAGING SYSTEM

CROSS-REFERENCES TO RELATED APPLICATIONS

This application is a continuation of U.S. patent application Ser. No. 15/860,346, filed on Jan. 2, 2018, entitled "Wide-Field Retinal Imaging System with Optical Coherence Tomography"; which is a continuation of U.S. patent application Ser. No. 15/228,669, filed on Aug. 4, 2016, now U.S. Pat. No. 9,872,618, entitled "Wide-Field Retinal Imaging System with Optical Coherence Tomography"; which claims priority to U.S. Provisional Patent Application No. 62/201,243, filed on Aug. 5, 2015, entitled "Wide-Field Retinal Imaging System with Optical Coherence Tomography"; the disclosures of all of which are hereby incorporated by reference in their entirety for all purposes.

BACKGROUND OF THE INVENTION

Retinal imaging relates to systems that capture a digital image of the retina, blood vessels, and optic nerve located at the back of the eye. These images can be used for the early detection and management of diseases of the eyes.

Although retinal imaging systems have been developed, there is a need in the art for improved methods and systems related to retinal imaging.

SUMMARY OF THE INVENTION

The present invention relates generally to methods and systems for optical devices. More particularly, embodiments of the present invention provide methods and systems related to retinal imaging with optical coherence tomography (OCT).

Embodiments of the present invention address issues related to sensitivity to scattering from the eye lens and cornea and provide a system characterized by small size, weight, and an appropriate physical configuration. Embodiments are characterized by no visible focused ghost images, low ghost background, and high resolution while achieving a wide-field imaging and field of regard to at least the equator. As described herein, embodiments provide uniform illumination and efficient use of illumination light, are able to be sanitized and have a form factor that enables insertion into small eye sockets. Additionally, embodiments enable the addition of image guided OCT while employing a design that avoids scattering and glare. These and other embodiments of the invention along with many of its advantages and features are described in more detail in conjunction with the text below and attached figures.

Embodiments of the present invention achieve wide-field retinal imaging with a camera that can be implemented as hand-held, that will image both pediatric and adult patients, and that will have an optional built-in light-weight image guided OCT and use a through the lens illumination system that is free from or reduces glare and reduces or minimizes scatter. Embodiments can be used with seated patients.

According to a specific embodiment, a wide-field retinal imaging system is provided that projects the retinal illuminating light through the imaging optics while obtaining high contrast, high resolution images with reduced or no glare from the imaging optics. Systems can be implemented as hand-held or table-top systems that are useful for supine or seated patients. In some embodiments, an image-guided optical coherence tomography (OCT) system is integrated into the retinal imaging system.

Embodiments of the present invention address one or more of the following issues:

Sensitivity to Scattering from the Eye Lens and Cornea

While children's crystalline lenses are in many instances very transparent, this is not always the instance. Adult eye crystalline lenses become progressively less transparent with age and back scattering can reach large percentages.

Small Size, Weight and Appropriate Physical Configuration

The camera can be comfortably held by one hand so that the second hand can be used to hold the patient's head or for other functions. Thus, the physical size is such that one hand can obtain a good grip on the camera body and that the weight is not unduly stressful for the clinician. In other embodiments, the camera can be mounted on a support.

No Visible Focused Ghost Images and Low Ghost Background

The light injection system does not produce "ghost" images (unwanted reflections from the optics, called "ghosts" because they are generally of lower light level). And for ghost images that are not focal, the level of the ghost reflection is well below that of the retinal light level.

High Resolution

Resolution of the optical system is high and meets or exceeds the ISO standards for retinal cameras.

Wide-Field Imaging and Field of Regard to at Least the Equator

Wide-field imaging is provided so that much of the retina can be captured with only a few images or an extremely wide-field single image can be obtained. Many of the clinical presentations in retinal care present wide-field such as diabetes, melanomas, retinopathy of prematurity, and so forth. A field-of-regard (FOR) to the equator is also provided.

Uniform Illumination

The irradiance on the eye should be uniform such that the variation of image brightness will be dominated by the regional reflectance of the retinal features and not the camera illumination pattern.

Efficient Use of Illumination Light

Efficient use of illumination light means that LED light sources can be used, thus avoiding the issues of high temperature bulbs such as Halogen and the need for bulky and fragile fiber optic cables between a light source and the camera. Because of the efficiency of an LED, the LED can reside in the camera housing instead of the control box, eliminating the large fiber optic cable. Second, efficient collection of light also means that the demands on the LED can be reduced.

Be Able to be Sanitized

The tip of the camera is contacted directly to body fluids and there is a risk of retaining pathogens that might be present in the patient's body. The system should be suitable for sanitation using common cleaning solutions such as Alcohol and diluted bleach.

Insertion into Small Eye Sockets

With premature infants especially, the eye socket can be small. This means that the camera tip should have a small diameter to reach to the cornea and for imaging to the periphery, it must be able to tip as well.

Addition of Image Guided OCT

OCT is a key technology for examining the layers of the retina and for determining the size of pathologies such as eye tumors. Being able to obtain OCT scans that are real-time image guided is a powerful tool and important dystrophies occur on a wide-scale in the retina such as for example retinal detachments. The use of this tool should become very prevalent in retinal surgeries.

To address these issues, embodiments of the present invention provide a camera that not only provides high-contrast and wide-field, but addresses one or more of the issues discussed.

According to an embodiment of the present invention, a hand-held imager for imaging the retina of the eye is provided. The hand-held imager includes an illumination source operable to generate illumination light and a beam splitter operable to receive the illumination light and direct the illumination light along an optical axis. The hand-held imager also includes a field lens disposed along the optical axis and an objective lens disposed along the optical axis and operable to contact the cornea of the eye. An aerial image is formed adjacent to the field lens. The hand-held imager further includes an image detector and one or more lenses disposed along the optical axis between the beam splitter and the image detector. The one or more lenses are operable to form an image at the detector.

According to another embodiment of the present invention, a retinal imager for imaging a retina of an eye is provided. The retinal imager can be hand-held or mounted on a support. The retinal imager includes an illumination source operable to generate illumination light and a beam splitter operable to receive the illumination light and direct the illumination light along an optical axis. The beam splitter can be polarized and/or can be a dichroic mirror. The retinal imager also includes a field lens (e.g., a plastic asphere) disposed along the optical axis and an objective lens disposed along the optical axis and operable to contact a cornea of the eye. An aerial image is formed adjacent to the field lens. The aerial image can be non-chromatically corrected (i.e., characterized by chromatic aberration) and curved. In one implementation, the field lens is disposed between the beam splitter and the objective lens.

The retinal imager further includes an image sensor and one or more lenses disposed along the optical axis between the beam splitter and the image sensor. The one or more lenses are operable to form a sensor image at the image sensor. The image sensor can be an array sensor. In some embodiments, the retinal imager can further include an OCT system coupled to the retinal imager.

According to yet another embodiment of the present invention, a method of operating a retinal imager is provided. The method includes positioning the retinal imager adjacent the eye of the patient. The retinal imager includes an illumination source operable to generate illumination light and an objective lens set including an objective lens (e.g., a single element objective lens) and a second lens. The method also includes bringing the objective lens in contact with a cornea of the eye and illuminating the retina of the eye with the illumination light passing through the objective lens set. The method further includes reflecting at least a portion of the illumination light off of the retina to provide a return signal, directing the return signal along an optical path, and detecting a sensor image at the image plane using an image sensor.

According to a specific embodiment of the present invention, a method of imaging a retina of an eye of a patient is provided. The method includes positioning a retinal imager adjacent the eye of the patient and obtaining a first image of a first portion of the retina, the first image associated with a central area (e.g., a circle) and a first field of view (e.g., 100 degrees). The method also includes obtaining a second image of a second portion of the retina, the second image associated with an annular area surrounding the central area. An outer periphery of the annular area is characterized by a second field of view (e.g., 130 degrees) greater than the first field of view. The method further includes combining the first image of the first portion of the retina and the second image of the second portion of the retina to provide a combined image of the retina.

In one implementation, obtaining the first image of the first portion of the retina comprises operating a spatial light modulator to illuminate the central area and block light propagating in the annular area surrounding the central area. Obtaining the second image of the second portion of the retina comprises operating the spatial light modulator to illuminate the annular area surrounding the central area and block light propagating in the central area. The spatial light modulator can be located adjacent an image plane of an image sensor.

According to a particular embodiment of the present invention, a method of forming a wide field of view image of a retina of an eye of a patient is provided. The method includes positioning a retinal imager adjacent the eye of the patient and obtaining a first image of a first portion of the retina. The first image is characterized by central area and a first field of view (e.g., 100 degrees). The method also includes obtaining a first additional image of a first additional portion of the retina. The first additional image is characterized by a first azimuthal range covering a first portion of an annular area surrounding the central area. An outer periphery of the annular area is characterized by a second field of view (e.g., 150 degrees) greater than the first field of view.

The method further includes obtaining a second additional image of a second additional portion of the retina. The second additional image is characterized by a second azimuthal range covering a second portion of the annular area surrounding the central area. Additionally, the method includes obtaining a third additional image of a third additional portion of the retina. The third additional image is characterized by a third azimuthal range covering a third portion of the annular area surrounding the central area. Furthermore, The method includes combining the first image of the first portion of the retina, the first additional image of the first additional portion of the retina, the second additional image of the second additional portion of the retina, and the third additional image of the third additional portion of the retina to provide a combined image of the retina.

BRIEF DESCRIPTION OF THE DRAWINGS

FIG. 1B is an optical schematic illustrating a classical through the lens imaging design.

FIG. 2A is an optical schematic illustrating delivery of light by means of a fiber optic ring lying outside the receive optical path.

FIG. 2B is an optical schematic illustrating return of the retinal reflectance for the system illustrated in FIG. 2A.

FIG. 4C is an optical schematic illustrating a non-contact illumination system.

FIG. 4E is an optical schematic illustrating a cross section of a contact through the lens imaging system.

FIG. 5I is an optical schematic showing additional detail of elements illustrated in FIG. 5H.

FIG. 7I is a schematic diagram illustrating the use of a spatial light modular at a sensor according to an embodiment of the present invention.

FIG. 14A shows a plot of RMS spot size at the retina for the sensor image at the image sensor according to an embodiment of the present invention.

DETAILED DESCRIPTION OF SPECIFIC EMBODIMENTS

Figure 1A:
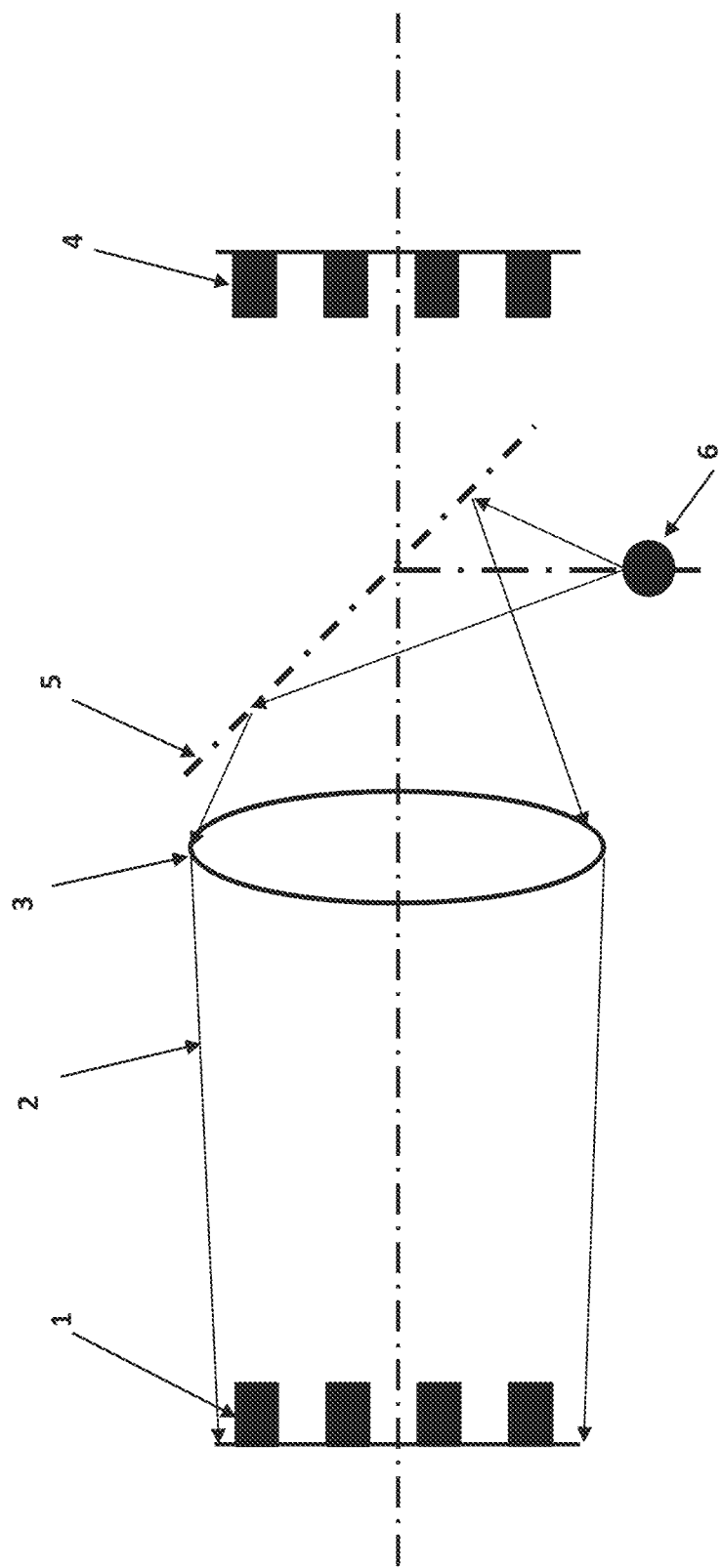
FIG. 1A is an optical schematic illustrating a classical through the lens illumination design.

In eye retinal care there are many instances where imaging most of but not necessarily all of the retina is sought. This is in contrast to traditional retinal imaging systems that typically only capture the posterior pole in a single image. One approach to achieve this is to develop a retinal camera with an ultra-wide field-of-view (FOV). There are however substantial limitations with such imaging and these are derived especially from the physical size and shape of the anterior of the eye and issues related to scattering and glare. Very few dystrophies are however present all the way to the ora serrati and cameras which achieve a modestly wide FOV have great utility.

In addition, in babies, and even many older pediatric patients, fall into the class of patients needing wide-field imaging but must be imaged supine. Some adult patients, especially while in surgery, would benefit from an imaging system that could be hand-held and wide-field and useable with the patient supine. Being able to mount such a system in a manner convenient for sitting patients would also be of value. While there is a commercially available wide-field retinal camera designed for hand-held use for pediatric patients only, this system faces serious limitations with image contrast, especially in eyes where the retina is darkly pigmented. Additionally, these systems, which may touch the cornea, will not work in a satisfactory manner with most adult patients.

In addition to classical bright field imaging and fluorescein angiography, optical coherence tomography (OCT) has become the standard of care and is seen as of equal value to conventional imaging. This points to the need for the provision of image guided OCT (where the bright field or angiographic image is displayed in real-time along with a marker on the image showing the location of the OCT scan). Embodiments of the present invention utilize OCT in conjunction with a vastly improved hand-held wide FOV imager.

Embodiments of the present invention provide enhancements over conventional hand-held OCT cameras that do not simultaneously provide bright field or angiographic imaging and have a heavy scan head.

The inventors have determined that while many physicians ask for "improved resolution" in many instances a better term would be "improved visibility." Higher resolution can be used in the sense of the performance of the optical lenses including the eye lenses to resolve two adjacent points. However, especially in the everyday clinic, the limit to visibility is frequently contrast, not resolution. It is relatively easy to design optics that on the ideal eye will have high resolution. It is, in comparison, very difficult to design illumination injection systems that deliver high contrast in the everyday clinic. In the clinic, on many occasions, only 80% of eyes image well, this limit arising from scatter in the human eye.

The level of difficulty of obtaining high contrast images of the retina can be understood by considering the low level of return of retinal illumination back to the camera. Retinal reflectivity can be as low as $10^{-3}$, the angular collection through the camera pupil is typically $10^{-3}$, giving a return of injected light of as low as $10^{-6}$. In some implementations, it is desirable to seek a total level of unwanted light below $10^{-7}$.

In imaging systems where the light passes through the camera optics on the way to the eye, the first challenge is to prevent unwanted reflections from the optics from entering the image. While this is not difficult in classical non-contact table-top cameras, these do not provide a wide FOV. These unwanted reflections are called "glare" or "ghost images." With high performance anti-reflection coatings, this return reflection is reduced to $5\times10^{-3}$ of the outgoing light and but this is a signal that can be much larger than the retinal return. Accordingly, the optical designer can use lens locations and curvatures such that the glare does not return to the image plane, especially as a focused or near-focused image, the so-called "ghost image". Additionally, the light injection must be such that the irradiance will be uniform on the retina and minimize scatter in the eye. For standard table top retinal cameras avoiding glare can be accomplished, but at the expense of narrow FOV and bulky size. However, in hand-held cameras that touch the cornea, this requirement is difficult to meet.

These through the lens retinal cameras are comprised of two optical systems that share the same space and lenses; one injects the illumination and one receives the light from the retina and forms the image. When OCT is integrated then three optical systems must generally be considered and these also share some of the same optics. FIG. 1A illustrates a classical through-the-lens-illumination system. Light source 6 injects illumination 2 through beam splitter 5 and light is collected by lens 3 and spread across object 1. Object 1 is a pattern of reflective linear strips interspersed with dark strips. FIG. 1B illustrates the imaging system comprised of the object 1, the collecting/imaging lens 3 and the typical return rays 7 are shown and form the image 4.

Figure 1C:
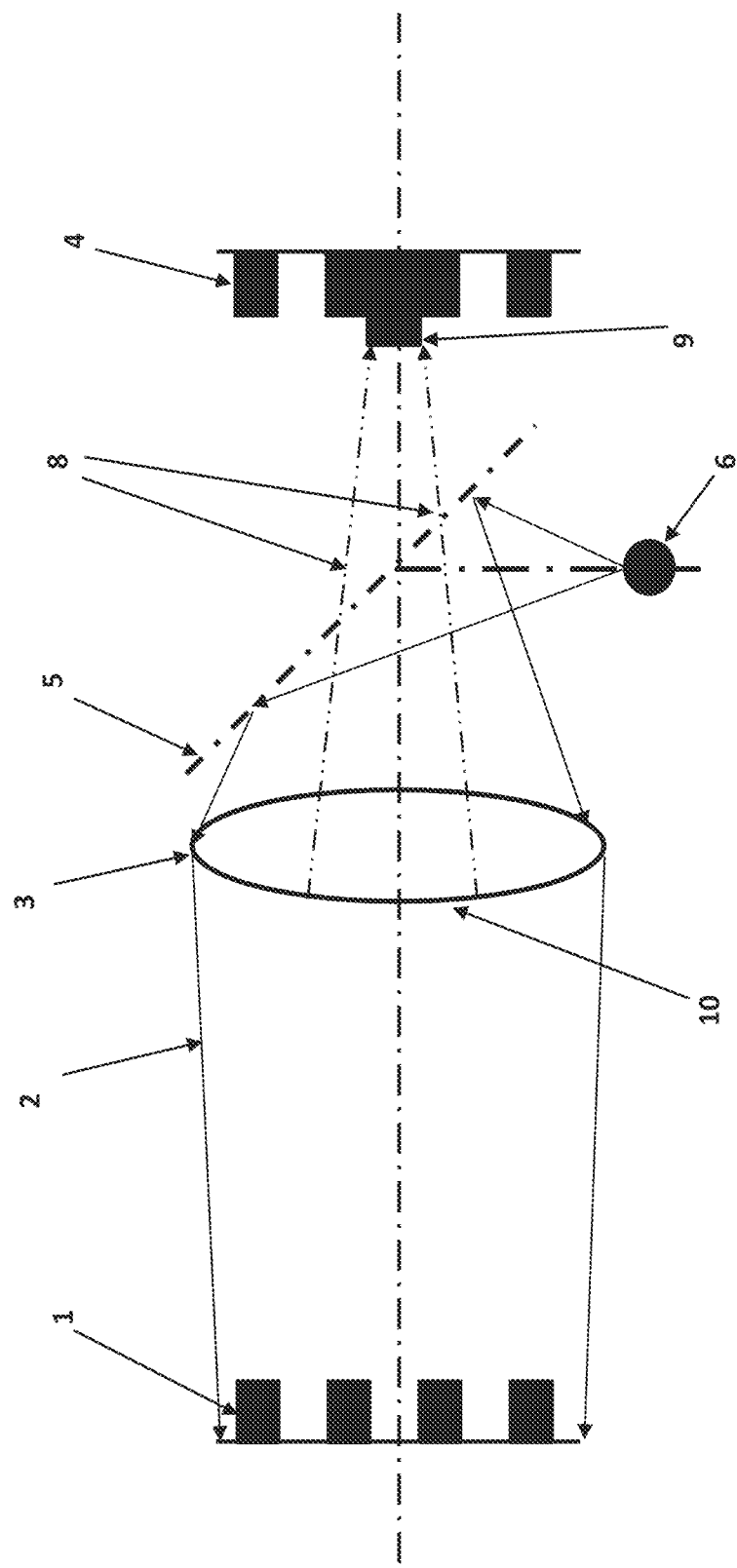
FIG. 1C is an optical schematic illustrating a classical through the lens illumination showing the effect of glare on the image.
Figure 1D:
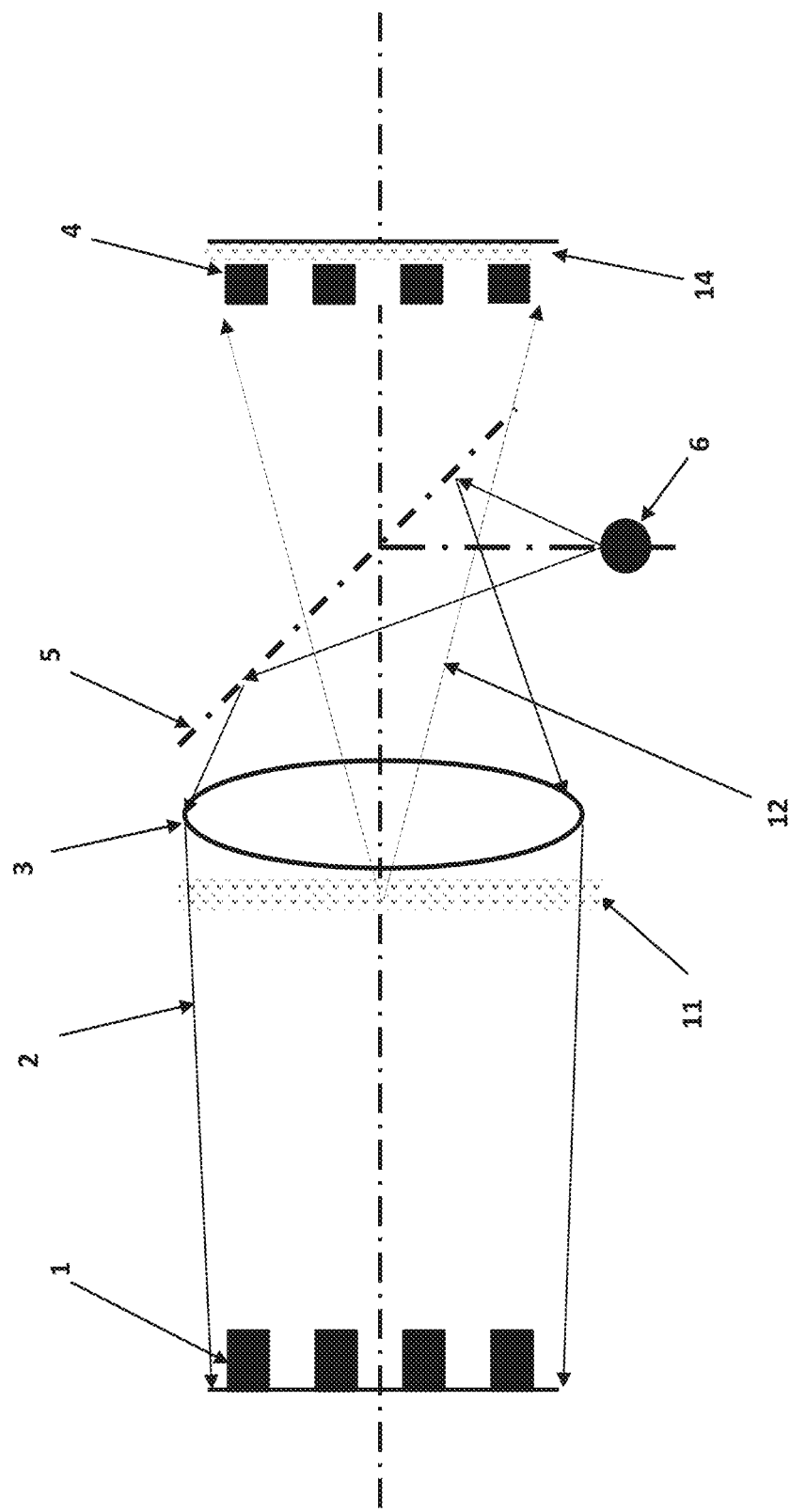
FIG. 1D is an optical schematic illustrating a classical through the lens illumination showing the effect of scatter on the image.

However, in this simplified optical system, neither glare nor scatter is considered. In FIG. 1C, glare is shown by optical rays 8 reflecting from lens surface 10 and striking detector plane 4 causing a ghost image 9. In FIG. 1D, a scattering medium 11 is present and illustrative rays 12 return to the image plane 4 causing a haze 14.

In imaging systems where the light passes around camera optics on the way to the eye, there is no glare, but the challenge is to prevent unwanted back scatter to the image. This class of cameras was developed to achieve wide FOV and in particular to deliver illumination to the retinal periphery and all this in a hand-held form factor. FIGS. 2A and 2B illustrate an around-the-lens illumination system. In this illumination system, the illumination light is delivered through a fiber optic bundle 15 surrounding the camera optics and specifically the contact lens 234 such that there is no glare, but this approach faces substantial challenges for uniformity of illumination and especially scatter 23. This system emphasizes the ability to direct light to the periphery of the retina 20. However as seen in FIG. 2A, if the iris 17 is not completely dilated, it can block the illumination rays 16 to the central portion of the retina 19, leaving a dark spot in the middle of the image. Since images are generally centered on the most interesting feature, this has proven to be a major objection to this camera.

Also in FIG. 2B is shown the imaging optical paths for receipt of light from the retina 21. Rays from the peripheral retina 20 exit through the entrance pupil 45 of the optical system and traverse first through the contact lens 234 and then through additional lenses to the image plane. A ray from the central eye retina 19, if it is illuminated, would also pass through the camera entrance pupil 45 and first through the contact lens 234 and then to the image plane.

However, as seen in FIGS. 2A and 2B, the eye crystalline lens 18 contains many scattering centers, which back scatter 23 the illumination light back through the contact lens 234 and on to the image and this serves as a key source of scattering that reduces image contrast in this design. Also in FIGS. 2A and 2B, where both the illumination and receive optical systems are shown side by side a boundary 22 is drawn on both images delineating the volume in the lens 18 where both the outgoing and return light pass together. In this design then nearly all of the light illuminating the eye passes through the crystalline lens 18 precisely in same volume 22 as the returning lights. From the viewpoint of reducing lens scatter, which is a major cause of low contrast images, such a design creates the highest possible scatter 23 from the eye crystalline lens 18 possible. As a consequence, retinal cameras with around the lens illumination have been very unsuccessful at producing high contrast images in a large percentage of pediatric patients and virtually all adult patients.

The inventors have determined that in many eyes the back scattering fraction is of a sufficient percentage such that when it is multiplied by the high level outgoing light produces a scattering return 23 that when compared to the low retinal return 21 destroys retinal contrast. Low contrast has a profound effect on the visibility of the key high spatial frequencies in the image. In this regard, for example, physicians want to detect tumors when they are small and a low contrast image inhibits this.

Figure 3A:
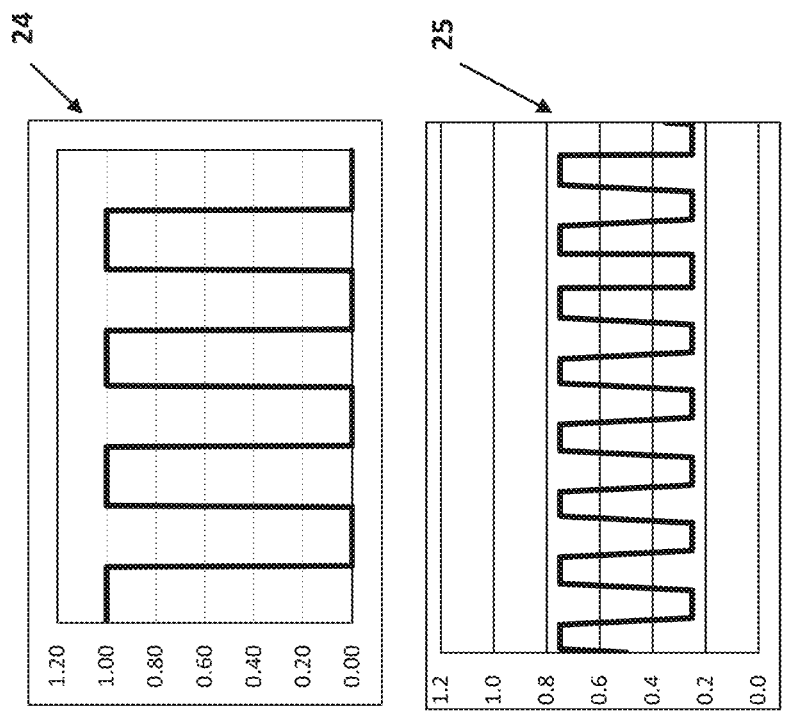
FIG. 3A is an image profile of a grating at low spatial frequencies and high spatial frequencies.
Figure 3B:
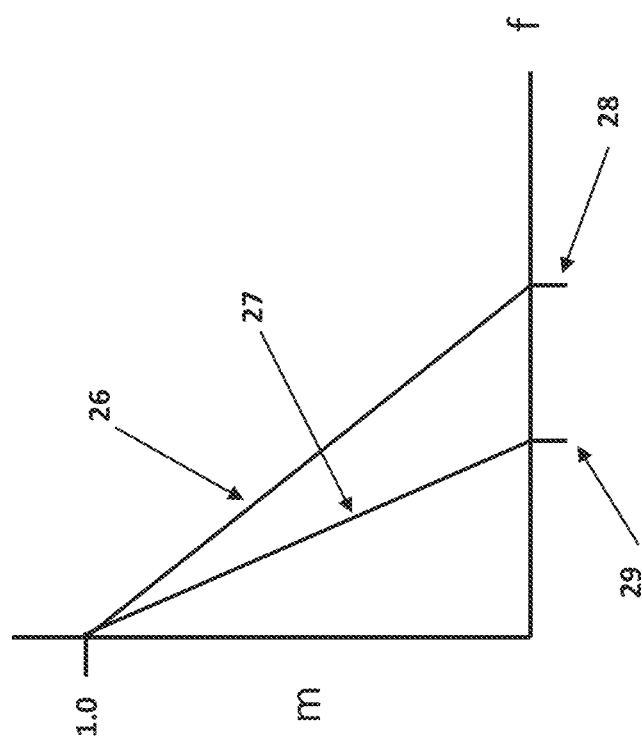
FIG. 3B is a plot showing CTF functional dependence as a result of optical resolution alone.

Referring again at the simplified through the lens illumination system optical system of FIG. 1B, this is comprised of a lens 3, an object 1, which is a reflective grating, and an image 4, which is a replica of the object subject to the imaging capability of the lens. In FIG. 3A, an image profile 24 is shown in which at low spatial frequencies the image quality is very good, but at high spatial frequencies 25, the image is degraded. This is of course driven by the imaging quality of the lens 3 and the limits of diffraction. A quantitative measure of contrast is the modulation index is defined as $$m = \frac{(Ix - Im)}{(Ix + Im)}$$

where Ix is the maximum intensity of the imaged pattern and Im is the minimum. This is a function of spatial frequency and is called the contrast transfer function (CTF). As shown in FIG. 3B, the CTF 26 declines with increasing spatial frequency f until it reaches a point where the visibility of the grating disappears 28. A typical lowest value of m at which the grating cannot be observed is m=0.3. For a lower quality lens, the plot might be 27 with a lower cut off frequency 29. While the CTF lines are show as straight for simplicity, they in general exhibit a more complex shape.

Figure 3C:
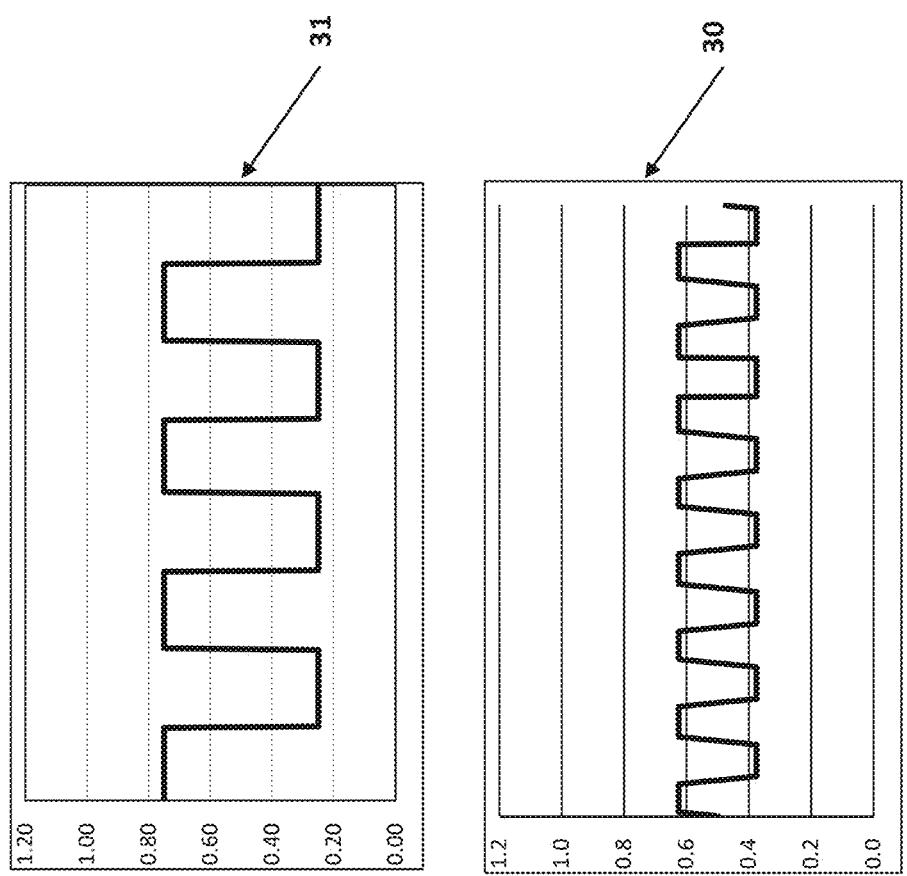
FIG. 3C is an image profile of low and high spatial frequency grating images with scatter of 50%.
Figure 3D:
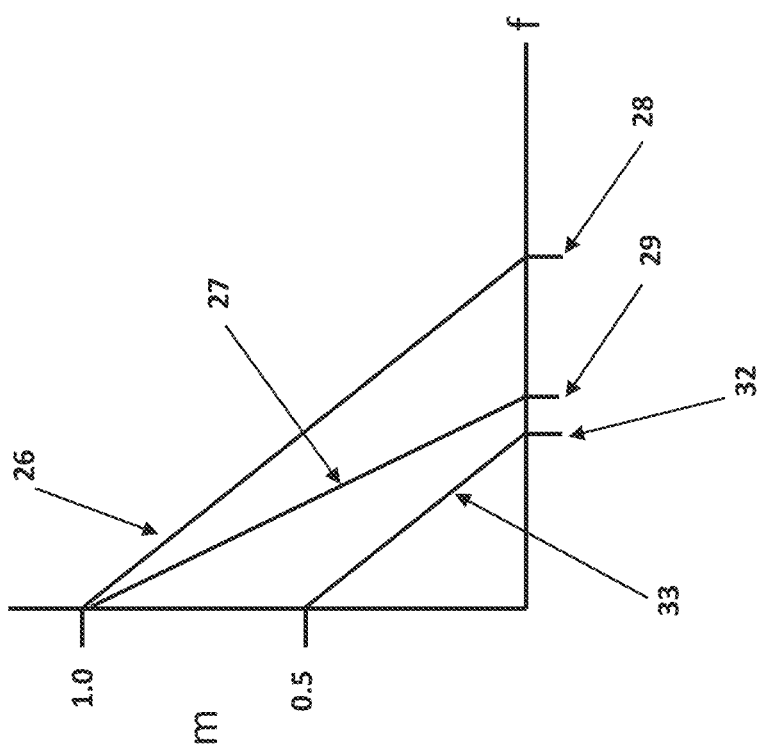
FIG. 3D is a plot showing a CTF function with and without scatter of 50%.

While attention is rightly focused on the limits to the CTF sourced by limitations of the optics, it needs to be recognized that scattering and the like reduces contrast in a similar way. To see this we introduce scattering as shown in FIG. 1D, where 11 is a volume containing material that scatters 12 and the scattered portion of the light at the image is 14. FIG. 3C illustrates the new image of the grating at the higher spatial frequency 30 and low spatial frequencies 31, both with scattering included. Note however that the high spatial frequency shown now has a modulation index m of 0.25, which falls below the visibility criteria of 0.3 and that at low spatial frequencies, the modulation index never reaches 1.0. In FIG. 3D, the high scatter transfer function 33 does not start at 1.0 and note that the cutoff frequency 32 is lower. The key issue is that the higher spatial frequencies are now not visible. The CTF with scatter can be modified from the CTF without scatter. The retinal return as a fraction of outgoing light is R, the back scattering of the outgoing light is S, and Ix is the maximum of the CTF with no scatter and Im is the minimum of the CTF with no scatter, then the CTF will follow as:

$$m = \frac{(Ix - Im)}{(Ix + Im) + S/R}$$

Accordingly, if the CTF with no scatter was 1.00 at low spatial frequencies and the backscatter was equal to the retinal return, then the CTF with scatter would be 0.5. And, when the backscatter was three times the retinal return, the CTF is reduced to 0.25 at low spatial frequencies.

With the experience that around-the-lens cameras cannot by design reliably generate high contrast images of pediatric or seldom do so for adult patients, attention needs to be drawn to finding techniques to utilize through the lens illumination. Accordingly, embodiments of the present invention achieve wide-field retinal imaging with a camera that can be implemented as hand-held or table top, will image both pediatric and adult patients, and that will have an optional built-in lightweight OCT using a through the lens illumination system that is free from glare or reduces glare and reduces or minimizes scatter.

In addition to achieving high resolution and high contrast images, embodiments of the present invention achieve high FOV or high field-of-regard (FOR). FOR is defined as the total accessible field of imaging whereas field of view (FOV) is defined as the instantaneous angular field of the image. The simple means of tilting the imaging hand piece to direct the center of the image to different portions of the retina accesses the various instantaneous images which together form the FOR. In particular, however, it is not necessary to achieve ultra-wide FOV capture in a single image. What is needed is an efficient means to capture a large amount of retina, but, if it were sufficiently efficient, then, the use of multiple images montaged together would be an attractive solution. Additionally, if these objectives were to be achieved in real-time, then the profound limitations of post-clinical session montaging could be avoided. Achieving this would radically change ophthalmic imaging but would only be valuable if a wide FOR was available.

Classical table-top based retinal cameras provide a field of view (FOV) of up to 60 degrees as measured from the entrance pupil. The efficiently accessed field of regard (FOR) is quite limited. A great deal of skill and patient cooperation is needed even for modest attempts at large FOR imaging. Typically, classical systems are table top systems that are not suitable for pediatric patients or supine adult patients.

Embodiments of the present invention meet the simultaneous challenges of imaging supine patients, in high contrast and high resolution, in a hand-held imager, and at high FOR/FOV, while also providing angiography and image guided OCT. Embodiments of the present invention are also of high value with seated adult patients.

Some systems transmit light through the cornea, but outside the image receive optical path. However, the major disadvantage, and one that prevents the use of this technology in many patients, is the lack of high contrast imaging as the design teaches away from high-contrast. A key feature of those designs is that light from one side of the eye is used to illuminate the retina on the opposite side, as shown in FIG. 2A. This is to allow illumination of the peripheral retina 20 perhaps not at the key center of the image 19 where light can be blocked by the iris 17. As for scattering the result is that the retina is indeed illuminated at the periphery of the field but the illuminating light crosses through the crystalline lens and through the volume 22 where light is returning from the retina to form an image. Thus, a great deal of the light passes through the crystalline lines in a volume 22 just posterior to the entrance pupil. The crystalline lens 18 is a major source of scattered light in the eye, in older patients this can be as much as 30% of the total light, and it is then collected with great efficiency through the exit pupil of the eye and profoundly reduces the image contrast. Thus, while this design eliminates the issues of ghost images from the camera optics or crystalline lens optics, it suffers from the worst possible sensitivity to scattering from the crystalline lens.

Indeed this device is seldom useful for adult patients since as the eye ages the crystalline lens develops more scattering centers. And, some pediatric patients have a lot of scattering from the crystalline lens giving a very low contrast image. Since some patients have dark retinas with a reflectivity over ten times below that of brightly pigmented retinas, the scattering is sufficiently high that these patients cannot be effectively imaged.

In contrast, embodiments of the present invention provide a wide-field retinal imaging system that does not suffer from ghost images or measurable contrast reducing scatter and produces quality images of patients with even darkly pigmented retinas, older eyes, or pediatric eyes with diseases that cause large increases in scattering.

Optical coherence tomography (OCT) is used to observe and document layers in the eye, tumors, and the like. The OCT scan is conducted using a low coherence optical source operating in the near infrared, which therefore is not visible to the eye. To circumvent this limitation, designers have resorted to acquiring a three-dimensional image, storing it, and then allowing the clinician to scan through the OCT image post imaging. This still does not give direct clues for the precise location of the 3D feature on the color retinal image. In contrast, embodiments of the present invention provide a real-time OCT scan location from the bright field, which is of enormous clinical value.

Embodiments of the present invention avoid scattering and glare using through the lens illumination, utilizing a through the lens hand-held wide-FOV retinal camera that produces high-contrast images of pediatric and adult patients and has a built-in image guided OCT and is light weight.

Glare: The Problem

Figure 4A:
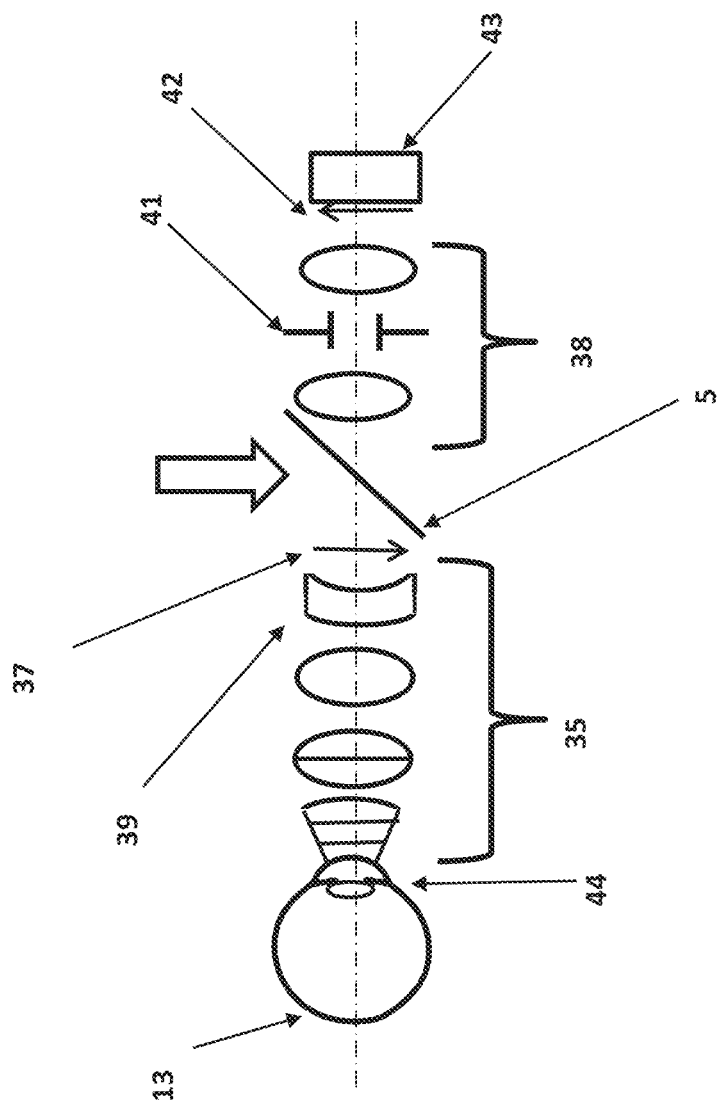
FIG. 4A is an optical schematic illustrating a corneal contact through the lens illumination system with imaging.

FIGS. 1A-1D discussed above addressed the generic issues of through the lens illumination systems. In a through the lens illumination system, glare from the camera lenses, the cornea, and the crystalline lens must be considered. FIG. 4A illustrates a through the lens contact imaging system using a classical contact imaging design. The object is to form an image 42 of the retina 13 onto the array sensor 43. The objective lens group 35 forms the first image 37. In the objective lens group 35 there is a triplet, a doublet, one singlet lens and a field lens 39. The objective lens group 35 forms a quality image at 37 so that the relay lens group 38 will deliver quality images 42 with any objective lens group 35. Objective lens groups with ultra-wide FOV and high magnification can be provided accordingly and interchanged.

Rear lens set 38 performs three key functions. First, it reimages the intermediate image 37 to the rear image 42 located at array sensor 43. Second, the relay lens group 38 provides focusing for the camera. Third, the rear lens group 38 has a Lyot stop 41 that is reimaged to the eye entrance pupil located at plane 44 and that forms the camera entrance pupil 45 (not shown here).

Figure 4B:
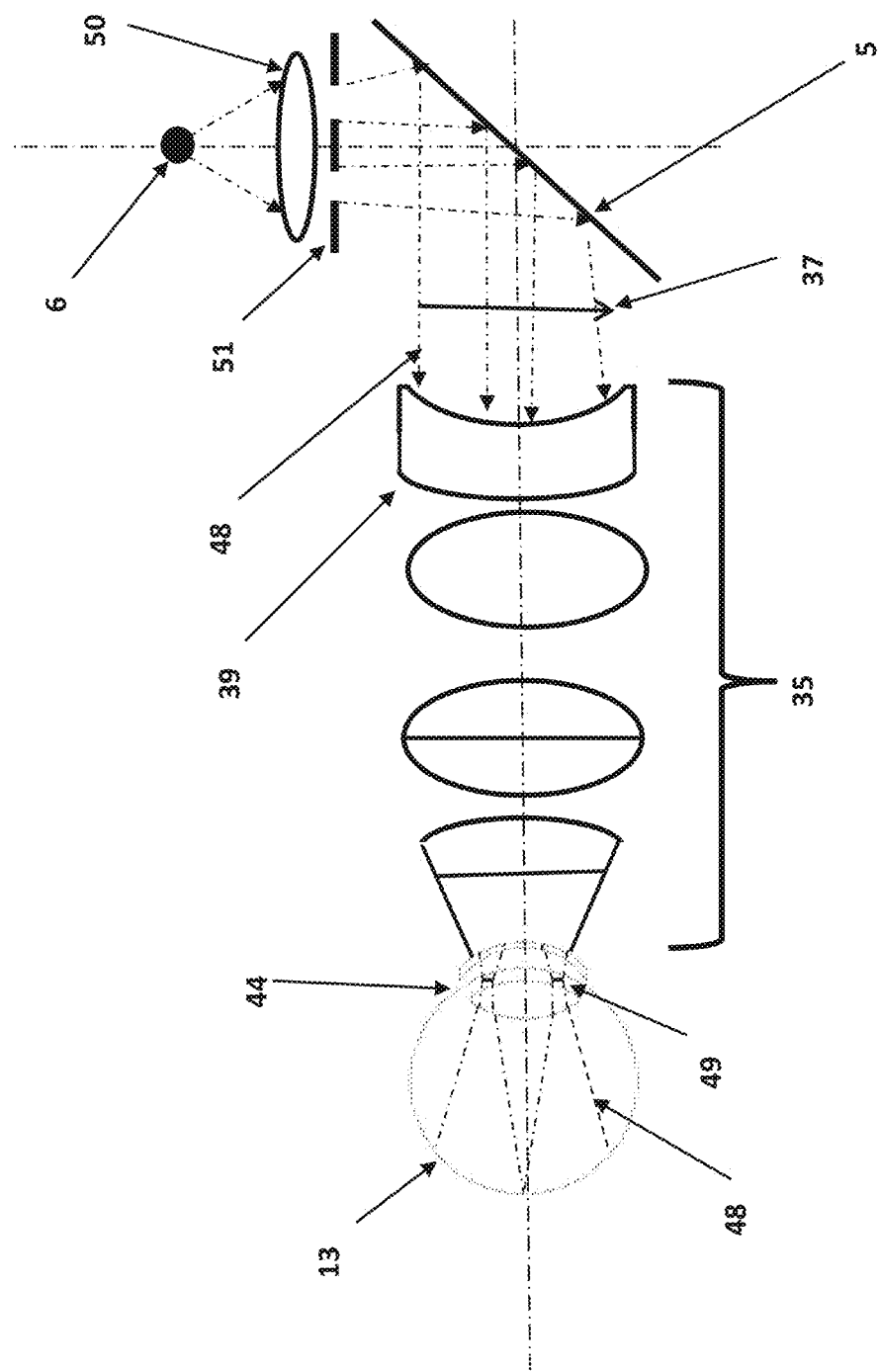
FIG. 4B is an optical schematic illustrating a corneal contact through the lens retina camera showing illumination paths only.

FIG. 4B illustrates a more detailed cross section of a through the lens illumination system, particularly the illumination paths. Light source 6 is injected by lens 50 through an annular mask 51, then through a beam splitter 5 and finally through the objective lens set 35 the (the complex paths of rays through 35 are not shown) and to the retina 13. The annular mask 51 is focused near the eye pupil plane 44 and diverges 48 to fill the eye.

FIG. 4C illustrates a cross section of a non-contact through the lens illumination system according to an embodiment of the present invention. The cross sectional view in FIG. 4C shows the relayed image of the annular mask 49 (a ring of light), which then expands 48 to illuminate the retina 13. The light returning from the retina 13 is bounded by return rays 47 and passes through the entrance pupil 45 of the camera (the image of the Lyot stop 41 and on to the image sensor 43, which can also be referred to as an array sensor since it can be implemented using a CCD or another appropriate imaging device. Note that region 58 is a volume of space in front of the cornea 59 for which the illumination light directed to all parts of the eye comes into a small bundle with intense irradiance, especially in the conical volume 36.

Figure 4D:
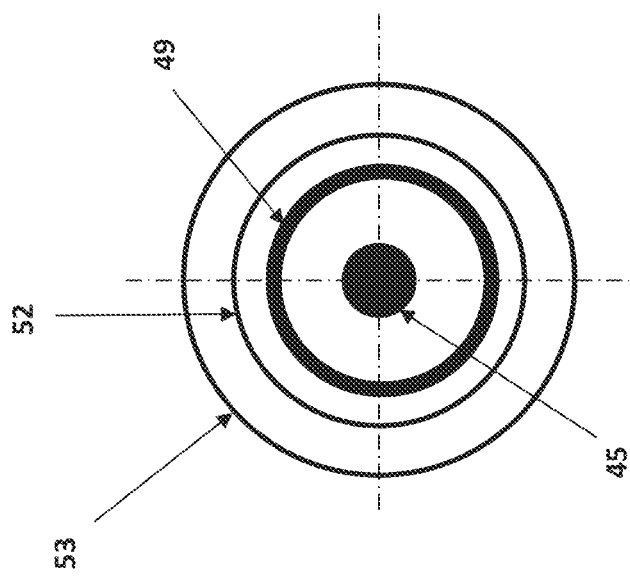
FIG. 4D is an optical schematic illustrating the front of the eye showing pupils and illumination.

FIG. 4D shows the front view of the eye in which 53 is the edge of the cornea, 49 is the annular light ring, 52 is the diameter of the eye pupil and 45 is the entrance pupil for the camera. FIG. 4E illustrates a cross section of a through the lens illumination system with a contact lens 434 in place. The illumination boundary rays 48 are shown and the front surface 56 has an intense illuminance, especially on the front surface 56 of contact lens 434. This intense irradiance at this lens presents a major challenge for corneal contact through the lens illumination systems due to reflections from the surface 56. As an example rays 55 are reflections from the front surface 56 of the contact lens 434.

Figure 4F:
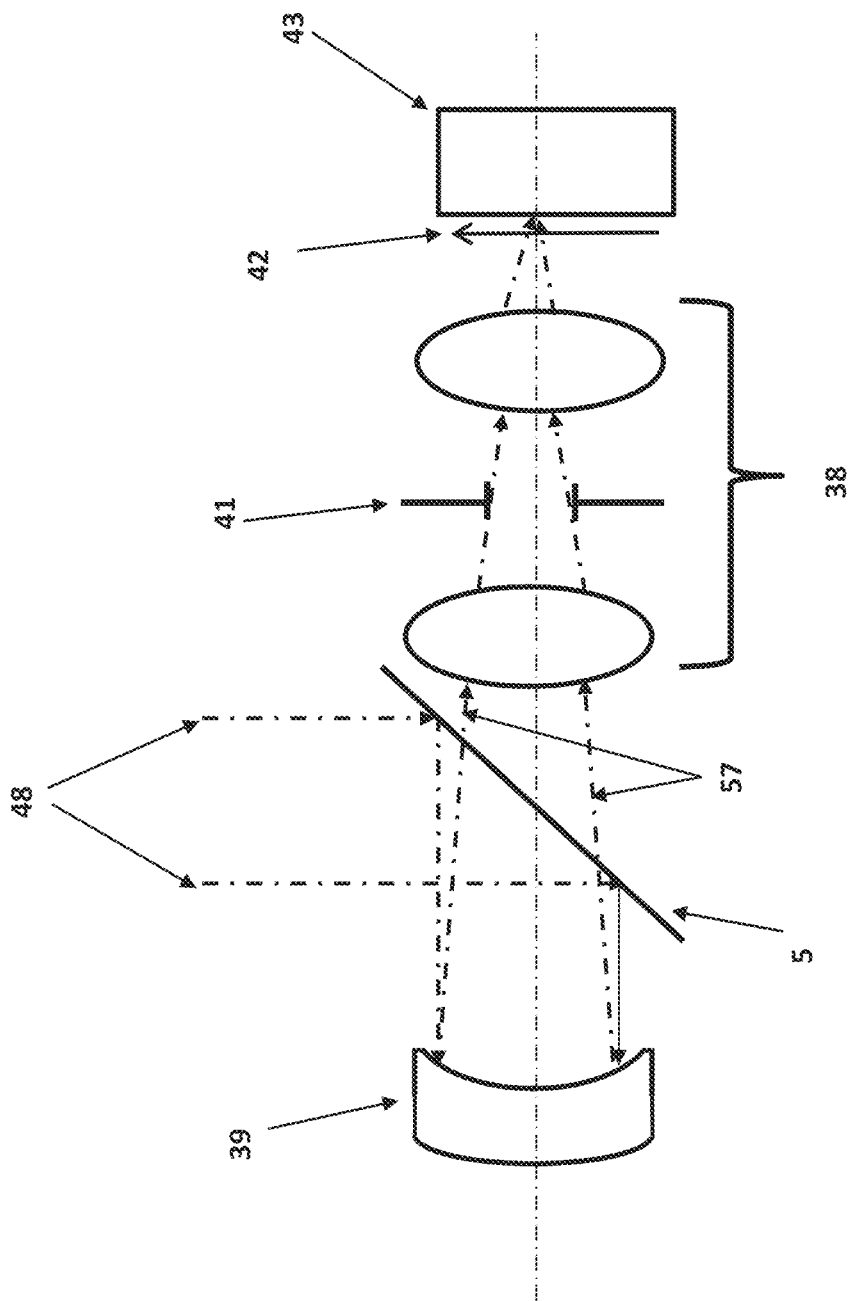
FIG. 4F is an optical schematic illustrating a through the lens illumination system showing issues of reflection from field lens with negative curvature.

The large ratio between outgoing and return illumination presents yet another challenge for glare in hand-held corneal contact retinal cameras. FIG. 4F illustrates the optical train of a classical through the lens illumination system and highlights issues of reflection from the field lens. In FIG. 4F, the last lens 39 in the objective lens set 35 is shown along with the rear lens set 38. This lens 39 at least partly serves the function of a field lens. A field lens sits at or near the focus and contributes little if any power to the system but directs the image rays into a small cone so that the rear lens set 38 can be of a smaller diameter. This is critical as the image 42 can be large and the return cone is highly divergent and without this, the rear lenses would have to have a physically large diameter. The rear lens set then in order to maintain reasonable f numbers would require a much larger size in terms of length.

However design principles for this system demand that this lens needs surfaces curved towards the image sensor 43. (While several lenses have this curvature and create problems, this one is especially troublesome.) Note in FIG. 4F, the ghost refection from the first surface of 39 directs ray 57 through the Lyot stop 41 and on to a ghost image at 42.

Figure 4G:
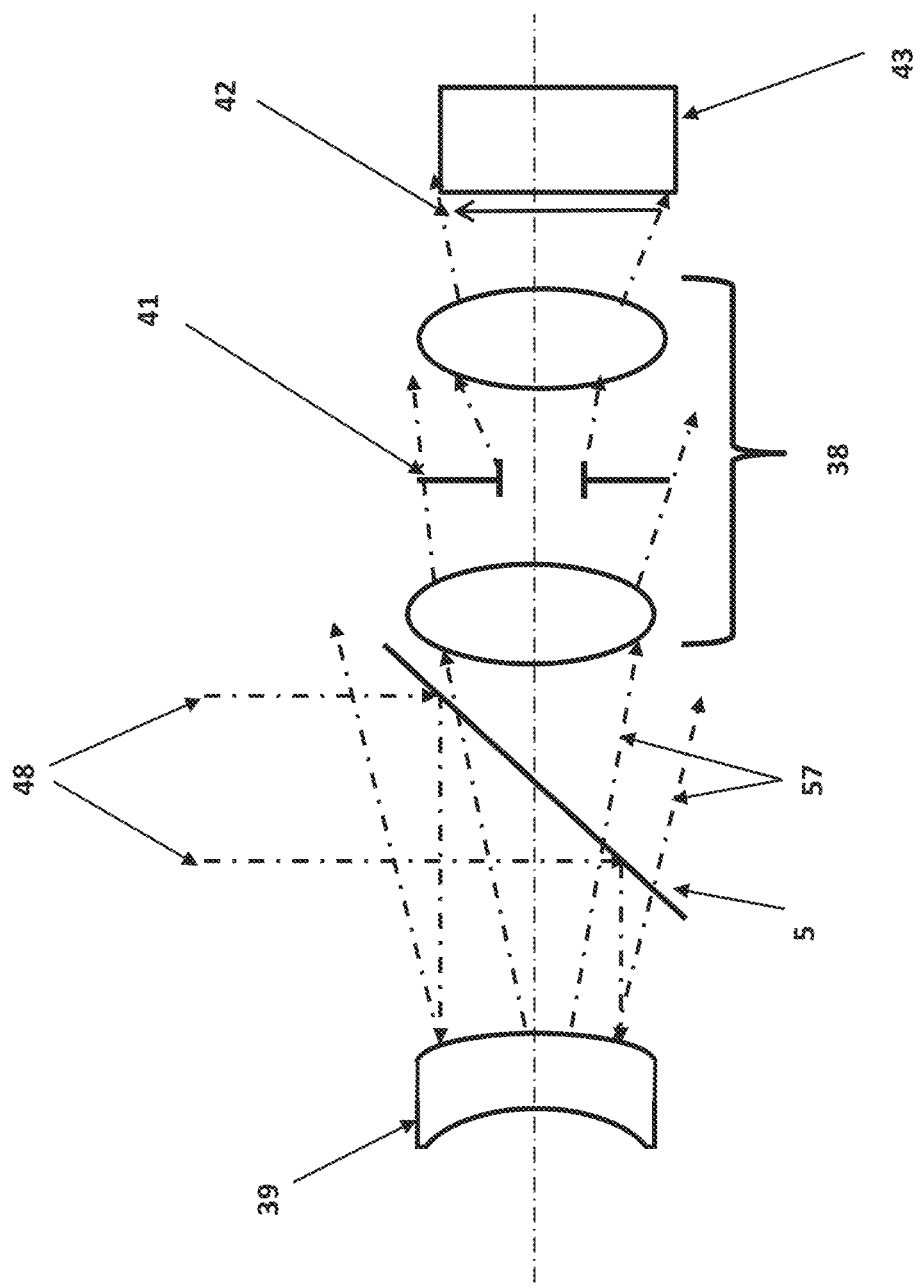
FIG. 4G is an optical schematic illustrating a through the lens illumination system showing issues of reflection from field lens with positive curvature.

FIG. 4G illustrates the optical train of a through the lens illumination system and highlights issues of reflection from a reversed field lens. In FIG. 4G, lens 39 has been turned around for illustration, demonstrating the point that the lens surface curvatures now in 39 creates a refection 57 whose diameter is very large. The Lyot stop blocks most of this and the irradiance per pixel at image sensor 43 is small and potentially non-significant. Clearly lenses with curvatures such as shown in FIG. 4F will create a significant dilemma for eliminating ghosts.

Referring once again to FIG. 4A, which shows the classical contact imaging lens format, fourteen reflective surfaces are illustrated:

The back of the eye crystalline lens
The front of the crystalline eye lens
The cornea, both surfaces
The contact lens
The bonded interface in the first bonded triplet
The rear glass to air interface of the first triplet
The front air to glass interface of the second doublet
The bonded interface of the second doublet
The front air to glass surface of the second doublet
The first air to glass surface of the singlet
The second air to glass surface of the singlet
The first surface of the field lens
The second surface of the field lens.

The need for a large number of optics for a quality image arises from the low optical quality of the human eye. While the resolution is high on axis (where reading occurs) towards the periphery, the resolution is very poor. And, the eye is not chromatic, the brain uses the longitudinal chromatic aberration to assist in focusing and the brain assembles the image in high quality. Thus, the camera designer is forced to use a substantial number of optics for high quality wide FOV imaging. As a result of the large number of optical surfaces, it is challenging or impossible to develop a solution characterized by no or reduced ghosts, uniform irradiance on the retina, and also high contrast.

Accordingly a first design principle utilized by embodiments of the present invention is that the number of lenses for which the illumination light is passed through will be reduced or minimized and that these surfaces will have the preferred curvature to prevent focused ghost images. This design principle lies in conflict with the requirement for high resolution images, uniform irradiance and a quality first image.

In order to accommodate the conflicting requirements for absolutely no or faint non-focused glare in a through the lens illumination system for wide FOV hand-held retinal imaging a new design concept has been implemented by embodiments of the present invention. If the issues of glare, especially for any lens close to the eye can be completely and absolutely removed, the design space for resolution, compactness, and illumination uniformity will be vastly enlarged.

Classical optical paradigms for design include an objective lens set that is required to produce a high quality image. Among other design precepts, it is taught in general optical design that the optics should not allow the red, green and blue rays to diverge in angle or ray height for any significant distance. The further into the beam train these proceed without correction the harder it is to put them back together. Note also that images must be flat to be applied to array sensors. The classical paradigms are seen evident in telescopes and microscopes.

Glare: The Solution

Figure 5A:
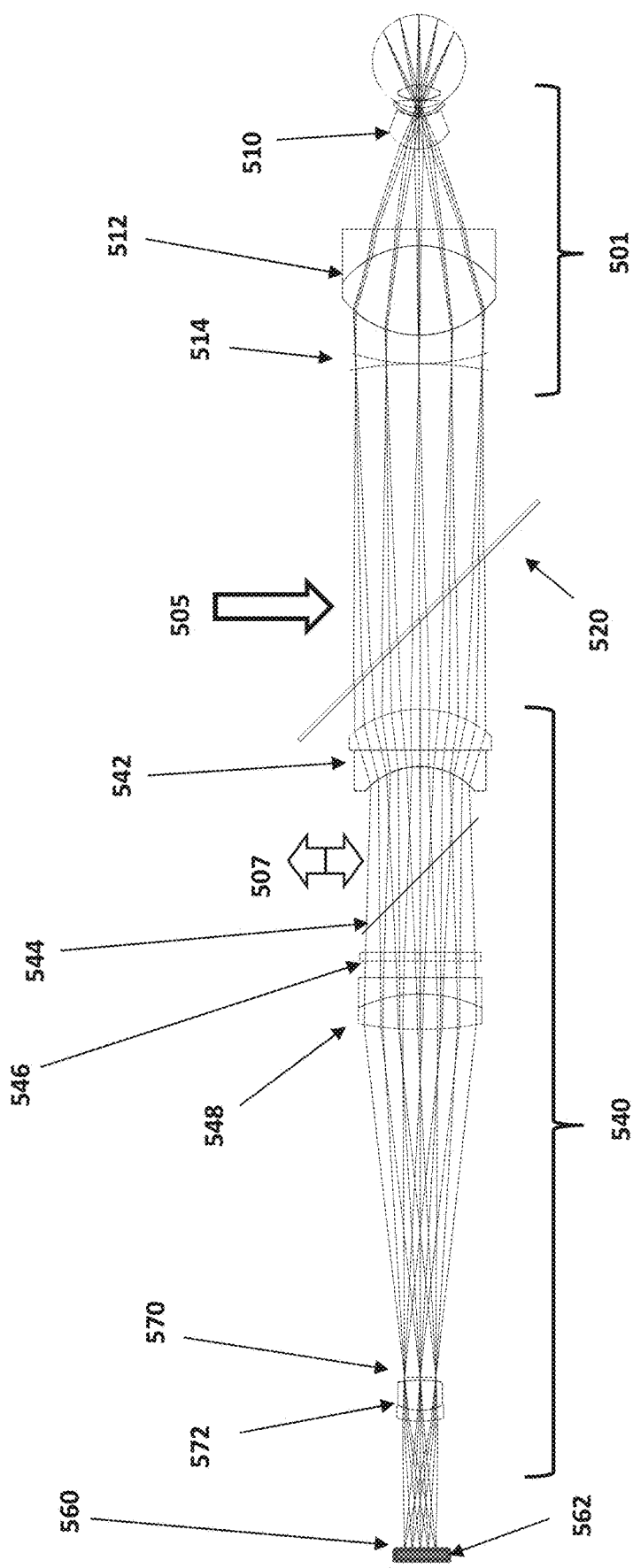
FIG. 5A is a corneal contact through the lens imaging system using a single objective lens according to an embodiment of the present invention.

Embodiments of the present invention utilize a design concept that differs from conventional optical design precepts. FIG. 5A illustrates a corneal contact wide-field imager according to an embodiment of the present invention. In the embodiment illustrated in FIG. 5A, a high resolution corneal contact wide-field imager is implemented with the unusual use of only one objective lens 510. This objective lens 510 does not have any surfaces negative towards the illumination source as they are objectionable for causing focused ghost images. The first image 514, which can be referred to as an aerial image, is shown as not achromatic, not high resolution, nor flat.

Figure 14B:
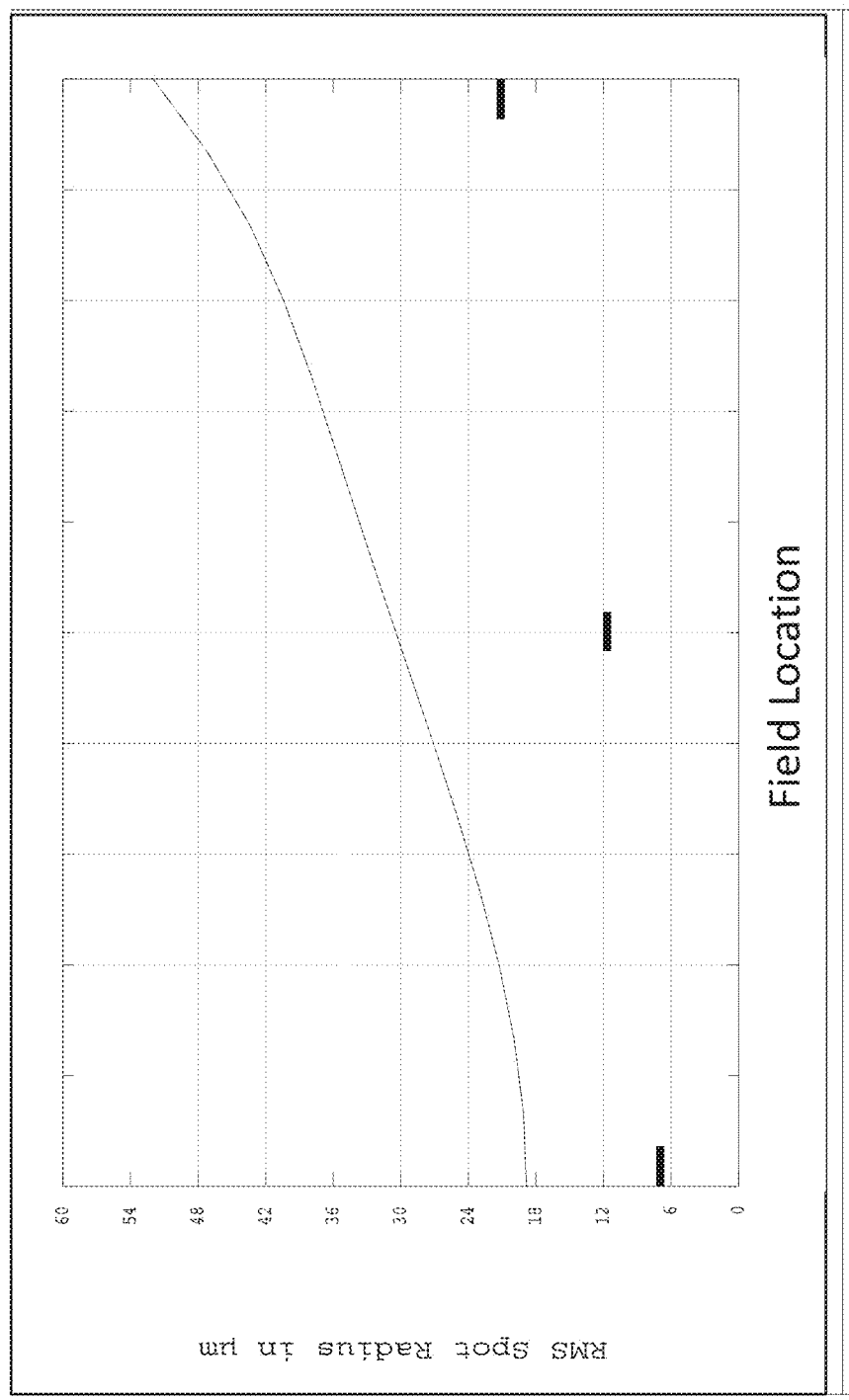
FIG. 14B shows a plot of RMS spot size at the retina for the aerial image according to an embodiment of the present invention.

FIG. 14A shows a plot of RMS spot size at the retina for the sensor image at the image sensor according to an embodiment of the present invention. FIG. 14B shows a plot of RMS spot size at the retina for the aerial image according to an embodiment of the present invention. Referring to FIGS. 14A and 14B, the RMS spot radius on the retina at the first image plane (where the aerial image is formed) as a function of field angle is shown in FIG. 14B. Retinal image resolution requirements are identified in ISO 10940 and these are noted on the plot as short dark horizontal lines and numbers are given from the central field, the mid-peripheral field, and the far peripheral field. For example, for wide field in the center of the image, the specification is 60 lp/mm or a spot size of 8 microns. At the edge, the requirement is 25 lp/mm or a spot size of 12 microns.

In all locations, the aerial image 514 fails to meet the standards of ISO 10940 by a large margin. By comparison, the image of the retina at the image sensor 562 (i.e., the detector) greatly exceeds the requirements as shown in FIG. 14A. Thus, the image quality of the sensor image at the image sensor, defined, by example, by ISO 10940, is greater than the image quality of the aerial image.

Figure 5B:
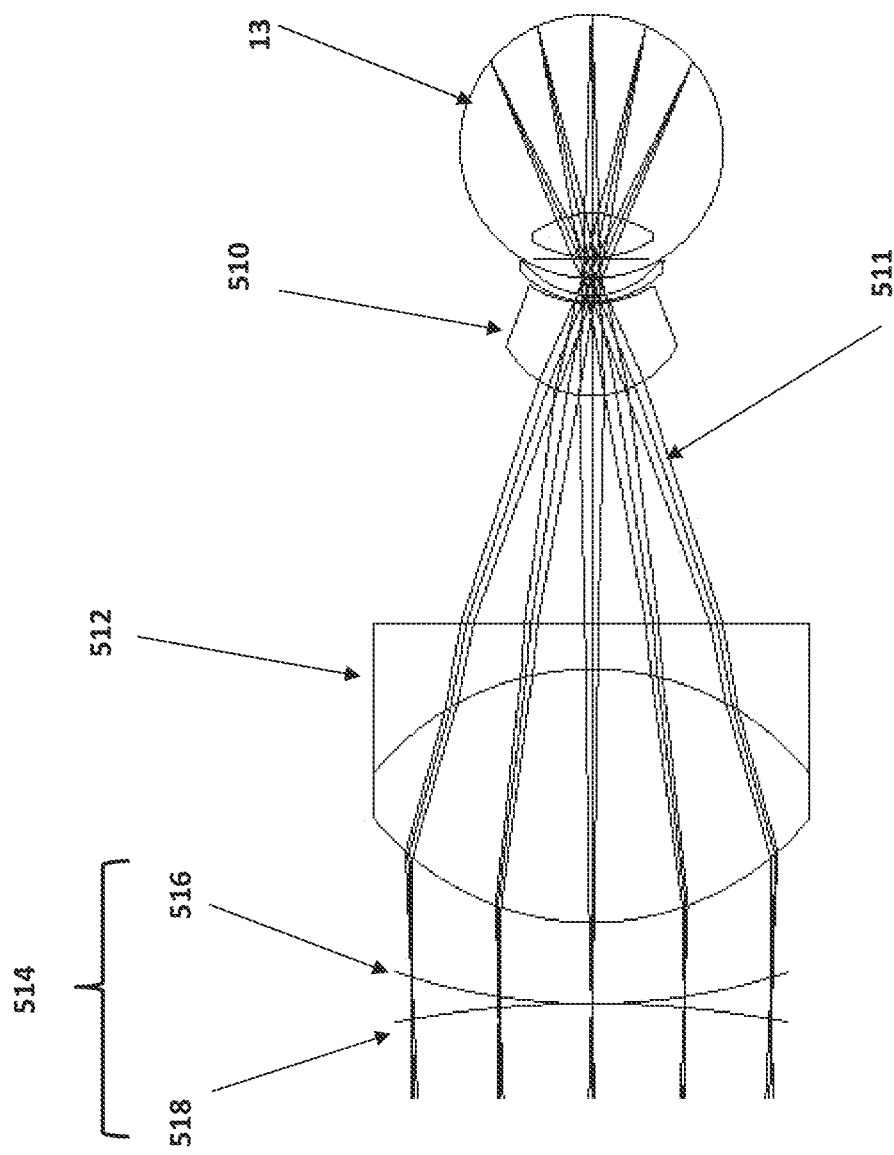
FIG. 5B is an optical schematic illustrating a corneal contact through the lens illumination system using a single objective lens according to an embodiment of the present invention including detail of a first image.

Indeed, as shown in FIG. 5B, the aerial image includes a tangential image 516 in FIG. 5B) and the sagittal image 518 in FIG. 5B) have millimeters or more of curvature at the edge and in different directions. Referring to FIG. 5A, the objective lens 510 (which can be the sole or only objective lens) utilized in the illustrated embodiment captures the light reflected from the retina 13, directing it in the direction of the image sensor 562, which can also be referred to as an image capture array, but not producing ghost images. The second lens 512, also referred to as a field lens, serves in part as a field lens and in part for image correction and is located within the illumination light 505 provided by an illuminator, also referred to as an illumination source (not shown).

Referring once again to FIG. 5A, the optical elements downstream of the beam splitter 520 can be referred to as an imaging lens group 540. Some of these optical elements are described in relation to FIG. 5C below. Beam splitter 544 is utilized to receive IR light from the optional OCT system and to transmit light to the OCT system. Thus, the OCT path is illustrated as optical path 507 in FIG. 5A.

Thus, embodiments of the present invention result in no or a reduced requirement placed on the quality of the first or aerial image. The high degree of optical correction is left to the rear optics lens set (i.e., imaging lens group 540), a concept either not recognized or believed to be not realizable. Note that embodiments of the present invention use 11 lenses (an achromatic is counted as two lenses) vs. conventional designs that can use 12 lenses. Accordingly, while embodiments teach away from standard design theory, these present embodiments illustrate that it is feasible and even with fewer lenses.

FIG. 5B illustrates the details of the objective lens set for the corneal contact wide-field imager shown in FIG. 5A. Rays 511 returning from the retina and through the object lens 510, which can be a contact lens, then pass through the second lens 512. These lenses could also be aspheric lens. Image 516 is the tangential image and 518 is the sagittal image. These images are each curved over a millimeter at the edge, giving over a 2 mm edge separation. By any standard, this is barely classified as imaging and the lenses 510 and 512 can be considered merely a light collection system rather than an imaging system. Not shown are the red, green and blue images, also lying in different focal structures.

Figure 5C:
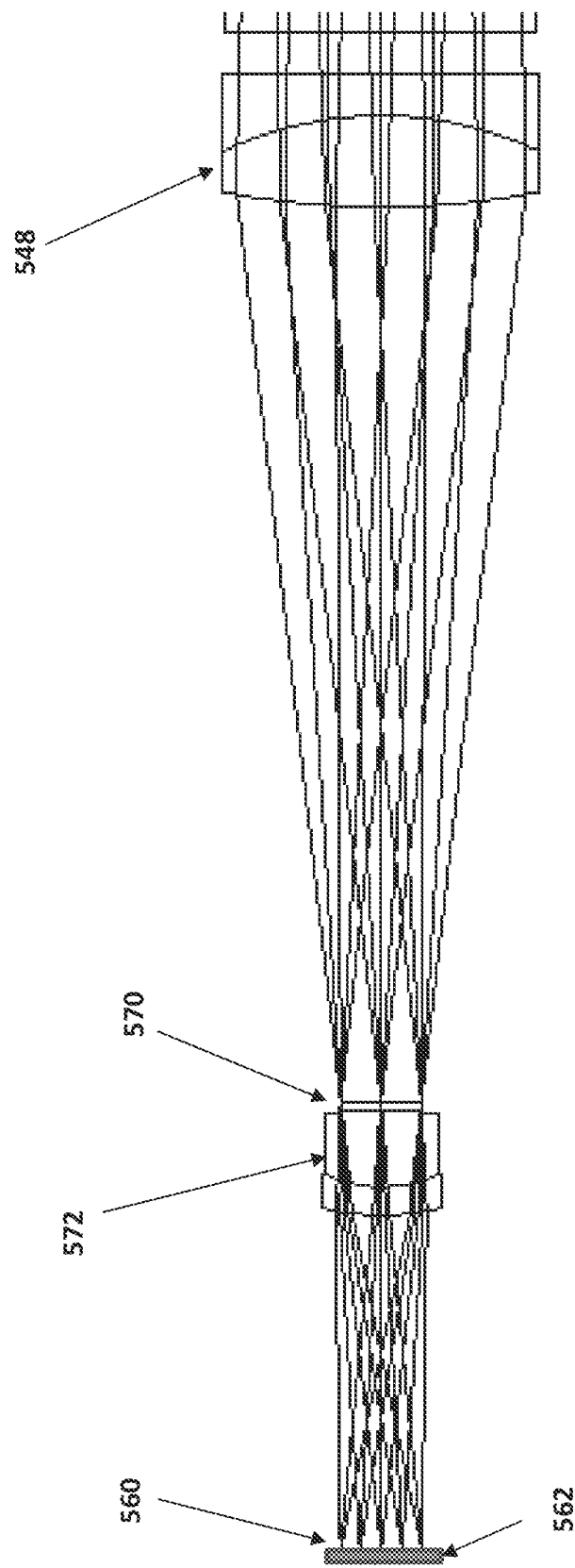
FIG. 5C is an optical schematic illustrating a corneal contact through the lens illumination system according to an embodiment of the present invention including details of a rear imaging system.

In FIG. 5C is shown details of the rear optics of the imaging system. Several of the optical elements illustrated as part of the imaging lens group 540 are illustrated in FIG. 5C. Lens 548 lies anterior to the illumination path and none of these lenses are subject to producing glare. The Lyot stop 570 lies just in front of the focusing lens 572, which forms the final and high quality image at an image plane 560, which lies in an image plane of an image sensor 562. Design codes suggest resolution at 3 microns and this is considerably improved over other wide-field cameras. Although only optical elements downstream of the beam splitter 544 are illustrated in FIG. 5C, it will be appreciated that other optical elements, including lens 542 can be utilized in the imaging lens group 540.

Figure 5D:
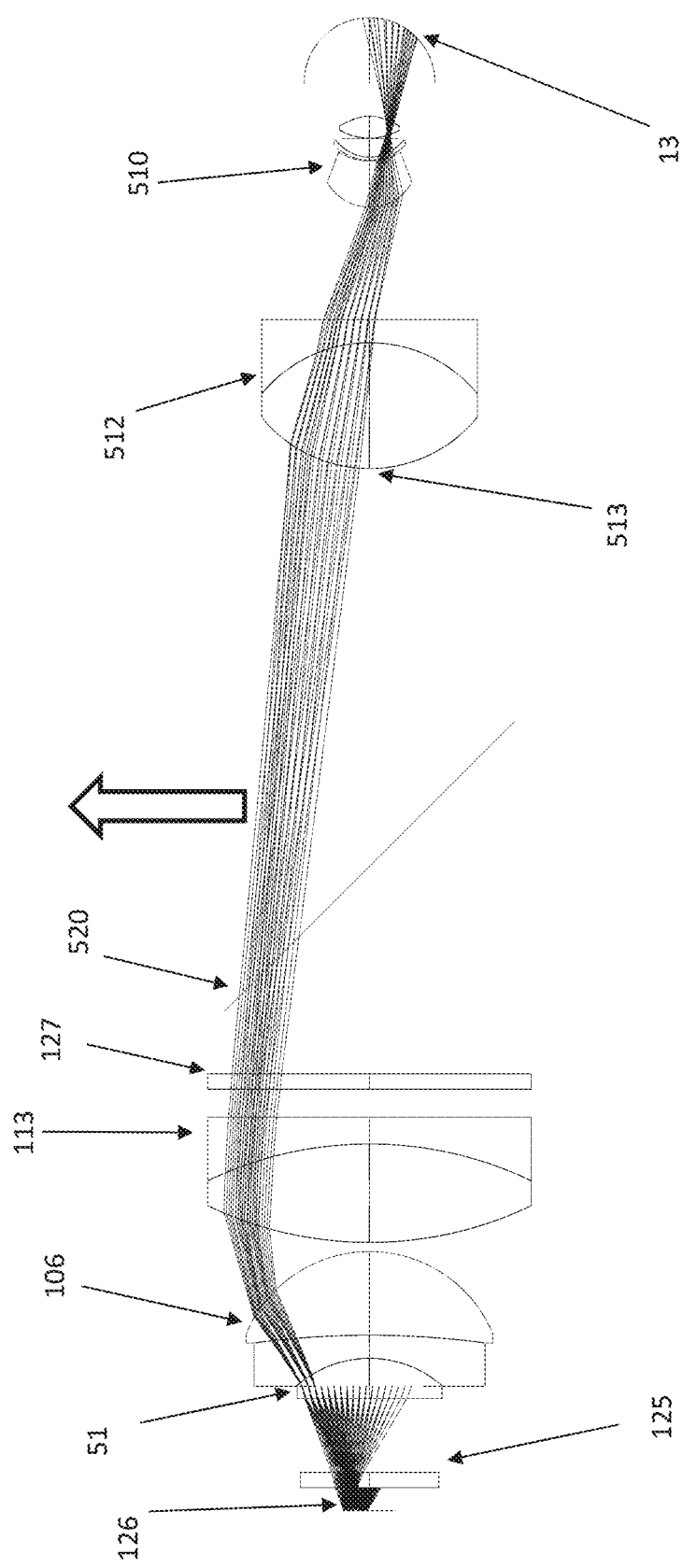
FIG. 5D is an optical schematic illustrating illumination optics of a corneal contact through the lens illumination system according to an embodiment of the present invention.

The detailed illumination format that is shown in FIG. 5D is a ring source but second lens 512 is far enough from the cornea that it avoids being in the region of high intensity illuminance 58 in FIG. 4C) in front of the cornea. In fact is it is close enough to the light ring source 51 that there is no illuminance at the apex 513 of the second lens 512, greatly aiding the prevention of ghosts. There is no glare returned to the image plane 560 by second lens 512, the objective lens 510, the cornea 508, or the eye lens (18 in FIG. 2A). Accordingly, embodiments of the present invention as illustrated in FIG. 5A can be characterized by no glints while producing wide-field illumination.

Referring once again to the illumination system shown in FIG. 5D, light source 126, which can be an LED, has a finite area and the light is first intercepted by mask 125, which contains a single block in the middle. The light is then intercepted by mask 51, which has an annulus opening to be imaged to light ring 49 in FIG. 6A). Lens 106 a doublet and doublet lens 113 constitute the illumination projection system. Item 127 is an optional excitation filter for angiography. Return light from the retina is intercepted by beam splitter 520. Second lens 512 and objective 510 also play a role in delivering light to the appropriate area the retina 13 with a high degree of uniformity of illuminance.

Figure 5E:
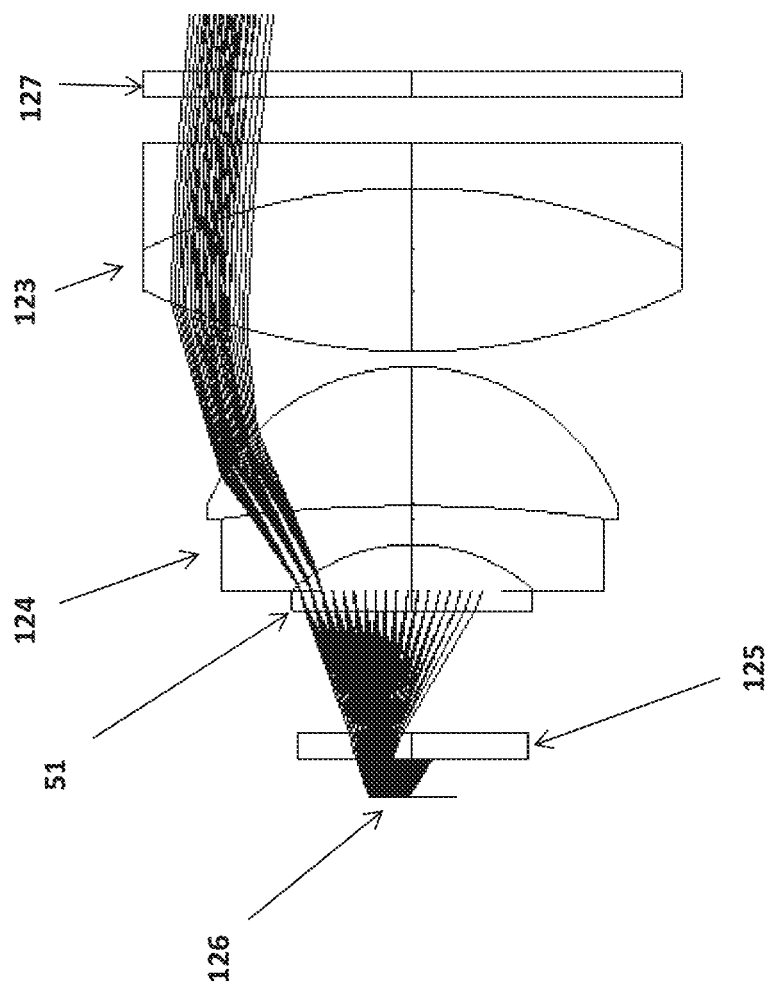
FIG. 5E is an optical schematic illustrating a corneal contact through the lens illumination system according to an embodiment of the present invention including details of illuminating optics.
Figure 5G:
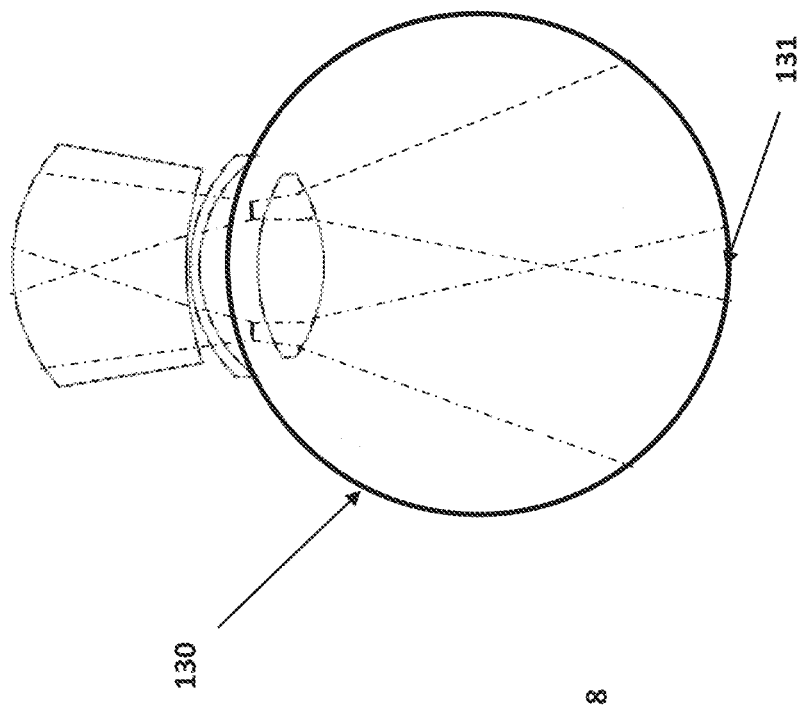
FIG. 5G is an optical schematic illustrating illumination ray boundaries for an eye of a second size according to an embodiment of the present invention.
Figure 5F:
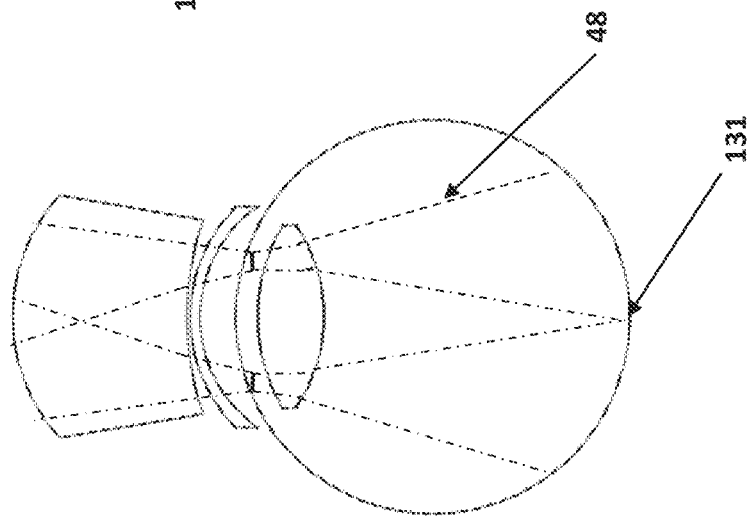
FIG. 5F is an optical schematic illustrating illumination ray boundaries for an eye of a first size according to an embodiment of the present invention.
Figure 5H:
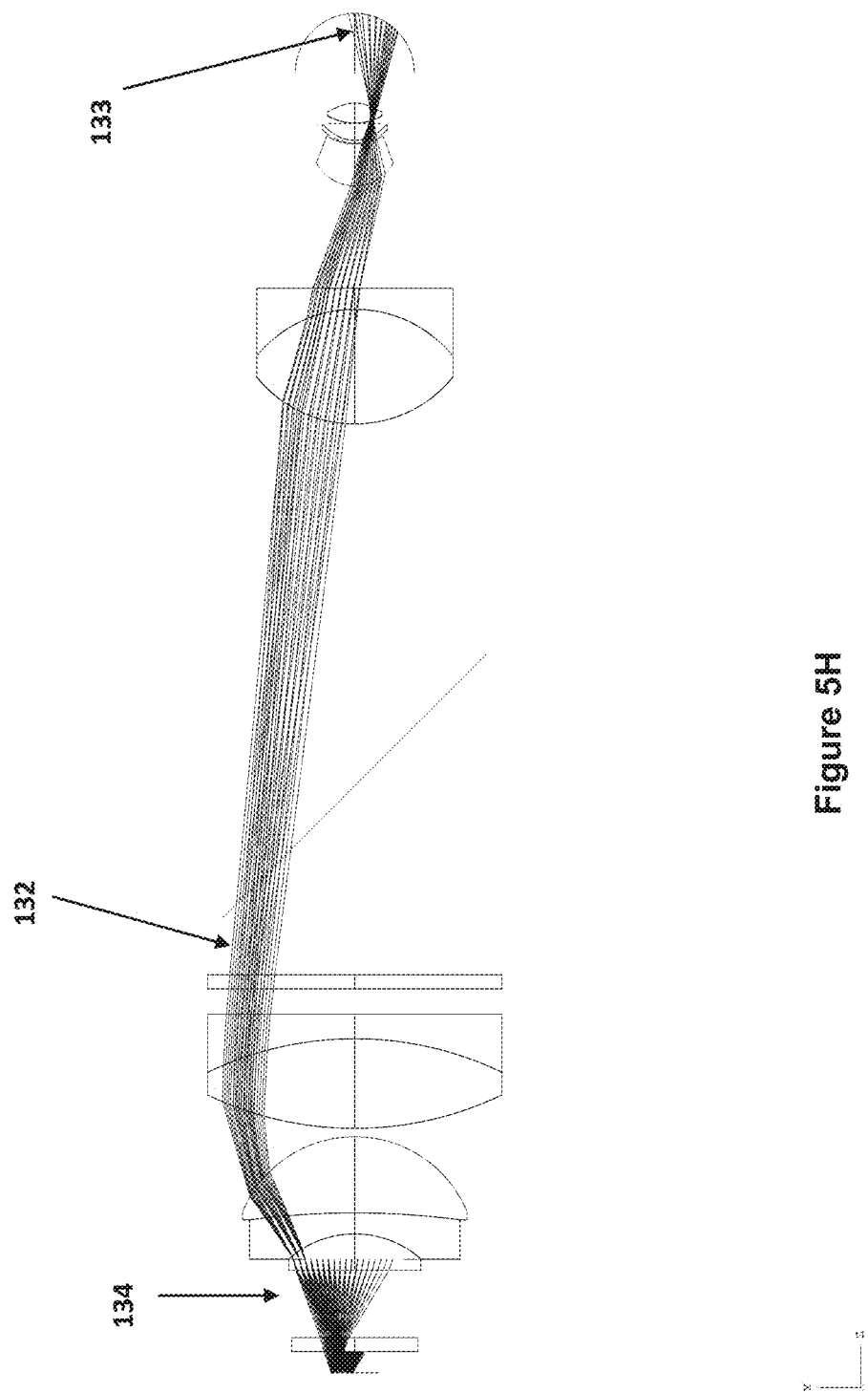
FIG. 5H is an optical schematic illustrating use of an iris to block outer rays according to an embodiment of the present invention.
Figure 51:
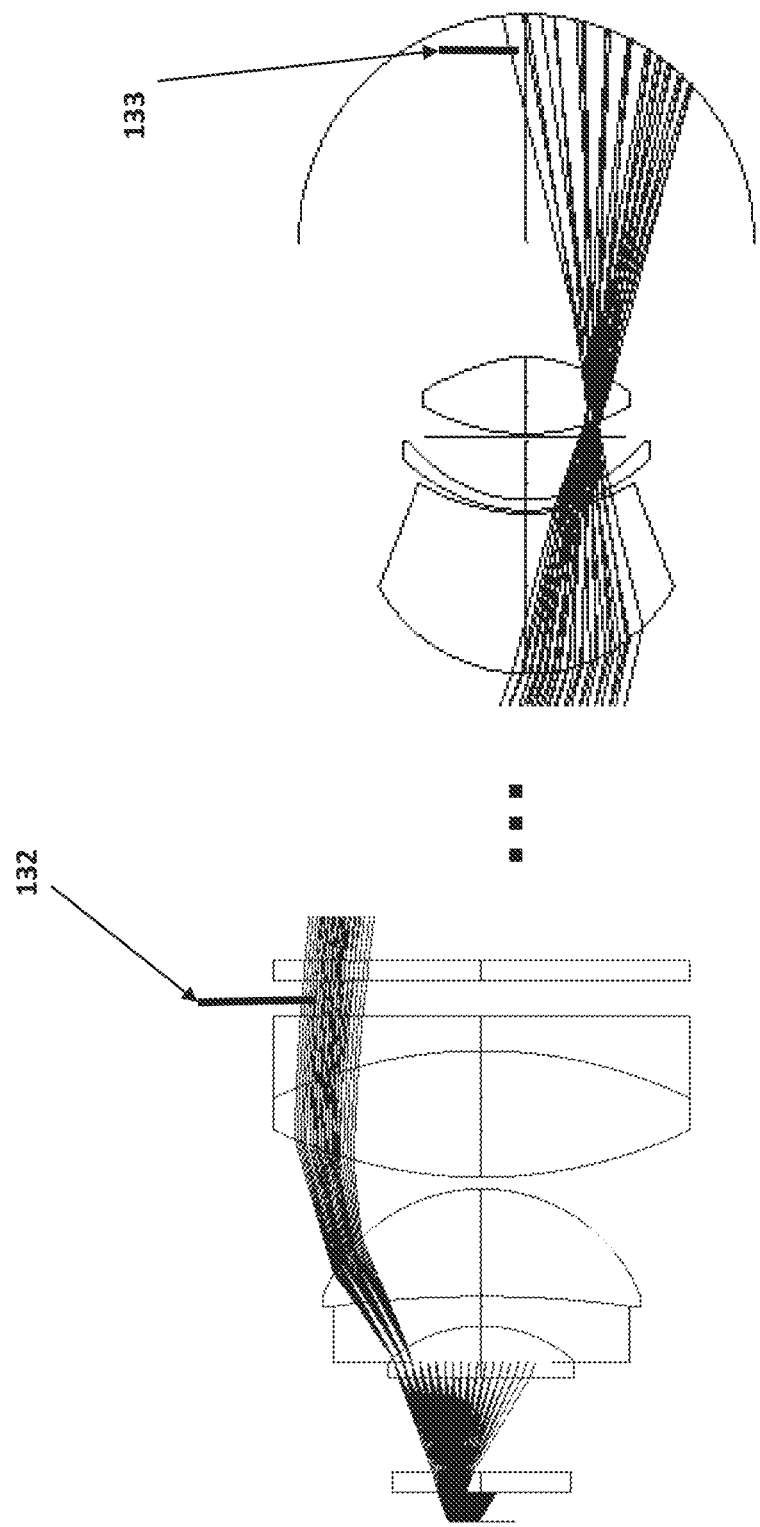

In FIG. 5E is shown a more detailed description of the front end of the illumination system. The illumination system produces uniform illuminance at the retina 13 when the diameter of the eye is known using lens 124 and lens 123 as well as other optical elements. For example as shown in FIG. 5F if the system is designed for the eye of the size illustrated in FIG. 5F, then the illumination rays boundaries 48 will just meet at the center 131 of the retina. However, as shown in FIG. 5G, if a larger diameter eye is present, then the rays 48 from both sides of the retina will overlap at the center 131 giving an irradiance "hot spot." This can be avoided by placing an iris at location 132 that can be set to block the outer rays 134 of the illumination bundle and therefore block the inner rays 133 at the retina. This is shown in more detail in FIGS. 5H and 5I.

Figure 5J:
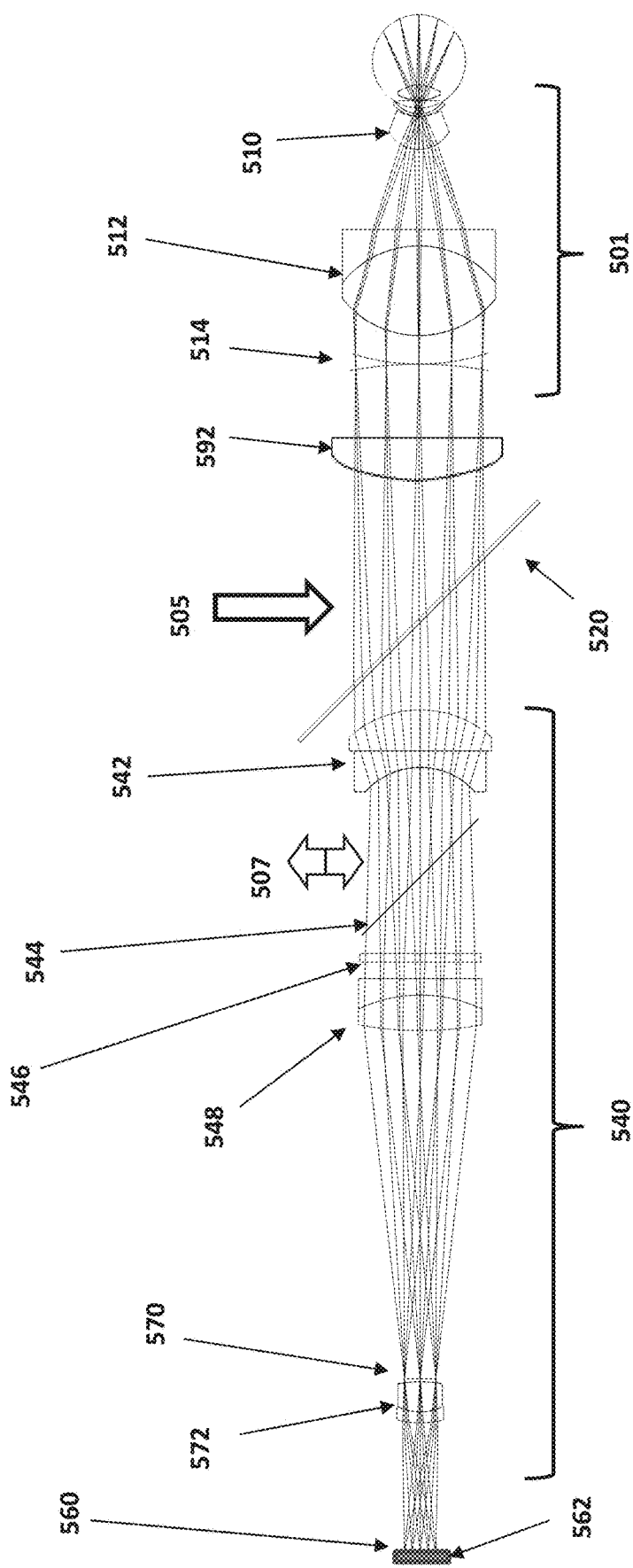
FIG. 5J is a corneal contact through the lens imaging system using a single objective lens according to another embodiment of the present invention.

FIG. 5J is a corneal contact through the lens imaging system using a single objective lens according to another embodiment of the present invention. The system illustrated in FIG. 5J shares common elements with the system illustrated in FIG. 5A and the description related to FIG. 5A is applicable to the system illustrated in FIG. 5J as appropriate. In FIG. 5J, an additional field lens 592 has been added between the second lens 512 and the beam splitter 520. In the illustrated embodiment, the additional field lens 592 is positioned between the aerial image 514 and the beam splitter 520.

Figure 10:
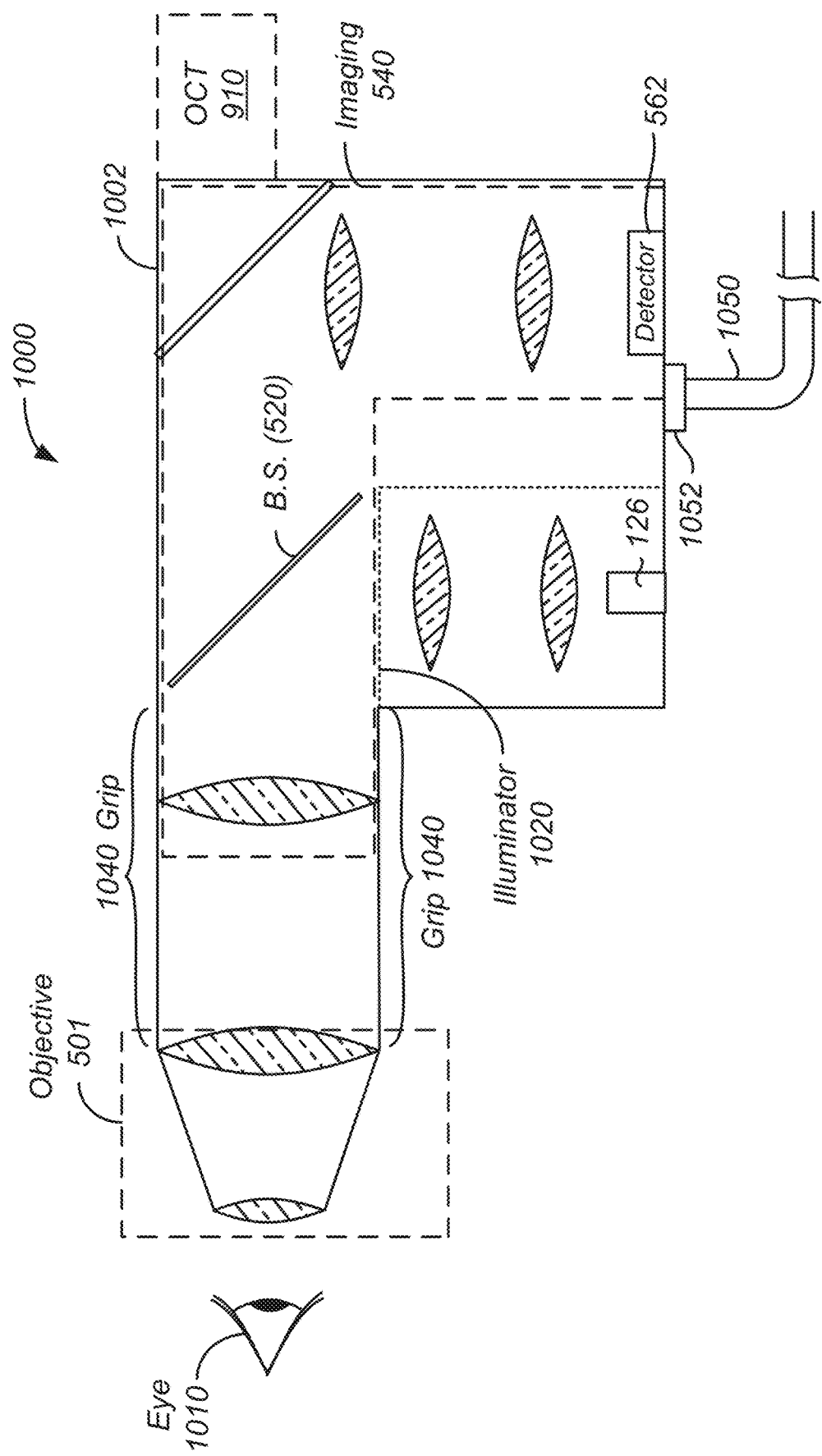
FIG. 10 is a simplified schematic diagram illustrating a hand-held imaginer for imaging the retina of an eye according to an embodiment of the present invention.

The utilization of the additional field lens 592 extends the distance between the second lens 512 and the beam splitter 520, which lengthens the grip 1040 illustrated in FIG. 10, making the hand-held imager easier to hold in a user's hand. Moreover, additional optics may be used without significant introduction of glare since the illumination beam in this region is a ring and easily reflects off the curved section of the lens to the walls of the camera, not entering back to the image plane. One of ordinary skill in the art would recognize many variations, modifications, and alternatives.

Scatter/Contrast: The Solution

The main sources of haze are scattering from the crystalline lens and the cornea and these backscatter at significant levels. In the human eye, the crystalline lens and the cornea have nominally equal back scattering per cubic mm. The cornea, while 200 μm thick, tends to back scatter more blue light. The crystalline lens may be as much as 2,000 μm thick, but, it will have proportionally less blue light scatter. Blue light scatter is the most significant challenge as this is dominated by Rayleigh scattering, which intensifies with the inverse fourth power of the wavelength. This scatter grows with patient age and this is why some retinal imaging systems are not applicable to adult patients.

Figure 6A:
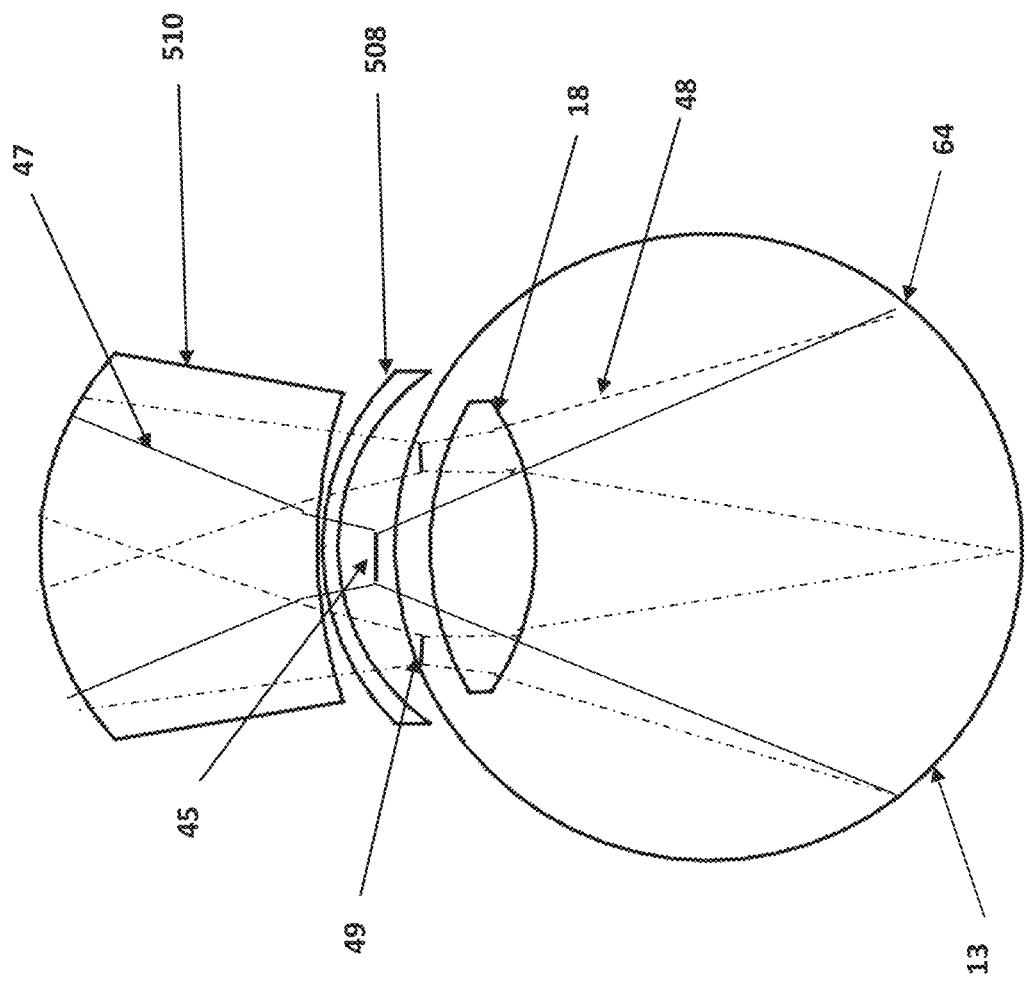
FIG. 6A is an optical schematic illustrating an eye profile view of a contact through the lens illumination system with objective lens at 100 degrees FOV according to an embodiment of the present invention.

FIG. 6A illustrates a cross section of the eye in a through the lens illuminations system using one objective lens according to an embodiment of the present invention. It should be appreciated that a clear gel including methocellulose, such as Gonak or Goniovisic, can be utilized between the contact lens and the cornea.

FIG. 6A shows the objective lens 510, the cornea 508, the eye crystalline lens 18, the camera entrance pupil 45, and the illumination ring 49. The input illumination bounded by rays 48 illuminates the retina 13 up to the point 64 which is at 100 degrees as measured from the center of the eye and the light is returned as bounded by rays 47, illustrated as rays 511 in FIG. 5B. The entrance pupil 45 of the imaging system is positioned between the lens 18 and the cornea 508. The illumination ring 49 is positioned at the front of the lens 18, parallel to the iris. Thus, the entrance pupil 45 of the imaging system and the illumination ring of the imaging system are offset longitudinally. In an embodiment, the longitudinal offset ranges from about 1 mm to about 5 mm, for example, 3 mm. The offset between the pupil and the illumination ring may allow designers additional margin when seeking to avoid the incoming light 48 from crossing an area when there is scattering tissue and the light can scatter back into the beam 47.

Figure 6B:
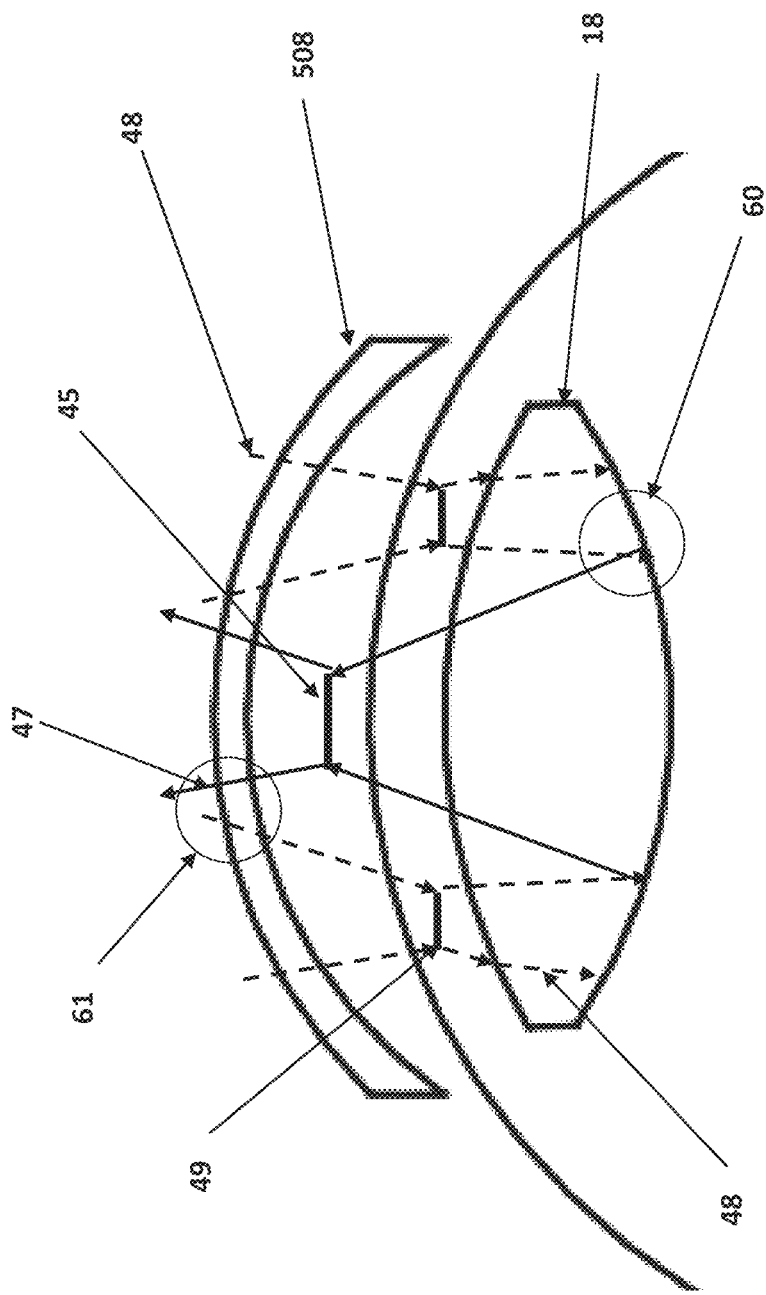
FIG. 6B is an optical schematic illustrating a detailed anterior segment view of a through the lens imaging system according to an embodiment of the present invention.
Figure 6D:
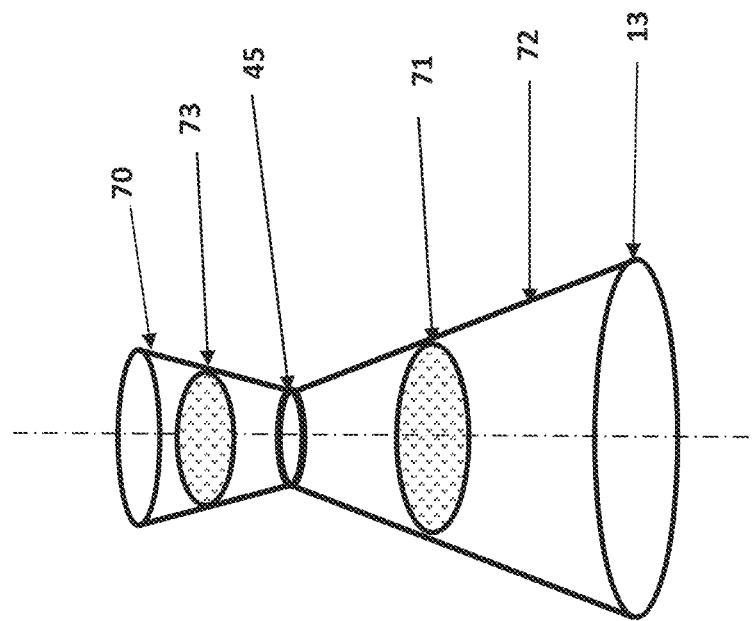
FIG. 6D is an optical schematic showing additional detail of elements illustrated in FIG. 6C.

FIG. 6B shows a magnified image of the anterior segment of the eye illustrated in FIG. 6A. The input illumination light is bounded by rays 48, the return light is bounded by rays 47, and the major scattering media the cornea 508 and the lens 18 are shown. The inventors have noted that the return rays delineated by rays 47 do not share the same space as the incoming rays delineated by 48 in the region of the cornea 508 or crystalline lens 18. Also, note the non-intersection area as marked by circles denoting volume 60 at the lens 18 and volume 61 at the cornea 508. This enables embodiments of the present invention to achieve a reduced amount of scattering or the lowest possible scattering.

In order for the scattering of the lens or cornea to enter into the image, the scattering centers must lie in the paths of the return light, which is not present in this design. The image produced by such a design will not be degraded by scattering in the cornea 508 nor the crystalline lens 18. It should be noted that the entrance pupil 45 and the illumination ring 49 are not located in precisely the same plane, but slightly offset longitudinally. By offsetting the illumination ring 49 and the camera entrance pupil 45 it is possible to achieve no scatting in the return light path 47 from either the cornea 508 or the lens 18. If the entrance pupil 45 was pushed anterior to lie in the iris plane with the illumination ring 49, then there would be scattering from the eye lens 18 and the cornea 508. If the entrance pupil 45 were pushed anterior, then there would be scattering from the lens 18. Indeed, many retinal images have an intense blue haze at the edge of the image.

Figure 6C:
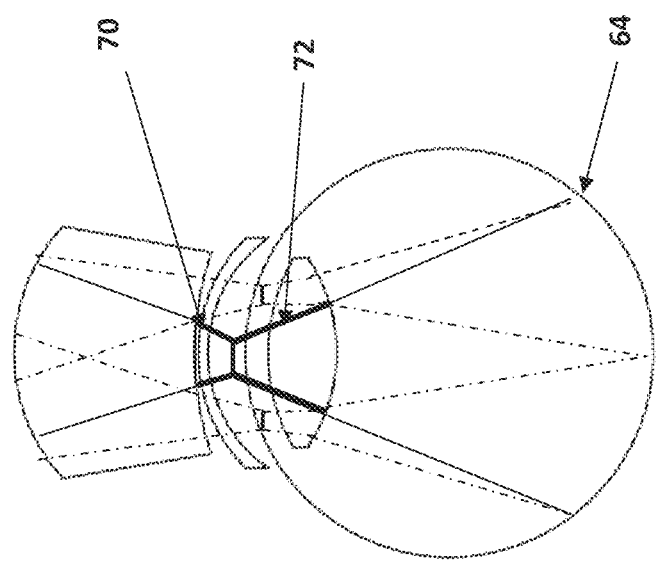
FIG. 6C is an optical schematic illustrating the concept of the "cone of silence."

FIG. 6C is a schematic diagram illustrating cones formed by light rays according to an embodiment of the present invention. FIG. 6C illustrates the cones of light above 70 and below 72 the entrance pupil 45. The inventors term this as the "cone of silence." According to embodiments of the present invention, a high contrast design is provided that does not place any illumination light in the cone of silence crossing any high scatter media 73 and 71.

First Solution to Scatter/Contrast while Imaging Nearly the Entire Retina: High Field of Regard For wide-field cameras, the best measure of FOV would be from the center of the eye. The covered retinal surface area scales with the square of the FOV as measured from the center of the eye whereas the covered retinal area has a non-linear relationship with the FOV measured from the entrance pupil. By this measure the FOV of the design shown in FIG. 6A is 100 degrees.

It has been common in ophthalmology for about fifteen years to in post-acquisition form montages of images obtained at different look angles. The technology for this has gradually improved but this is still a tedious task and is nearly always performed by ophthalmic technicians with a lot of training and rarely if ever by a physician. However, post-acquisition is always difficult as when obtaining a large set of images the clinician cannot typically determine if the set is good until leaving the presence of the patient. Indeed, this kind of work is usually accomplished by technicians at the end of the clinic day, good results are not frequently the case.

In contrast with these conventional systems, embodiments of the present invention form a mosaic of images in real-time as they are obtained. The images can be automatically obtained and merged on the fly or the user can provide an indication (e.g., press a button) when the best image at each look angle is obtained. Using this method, embodiments of the present invention provide revolutionary solutions for ophthalmic imaging.

According to the embodiments described herein, the FOV can be extended with perfect or near perfect rejection of scatter from the cornea and lens by obtaining segmented images in rapid succession.

Second Solution to Scatter/Contrast: Wider Field Images

Figure 7A:
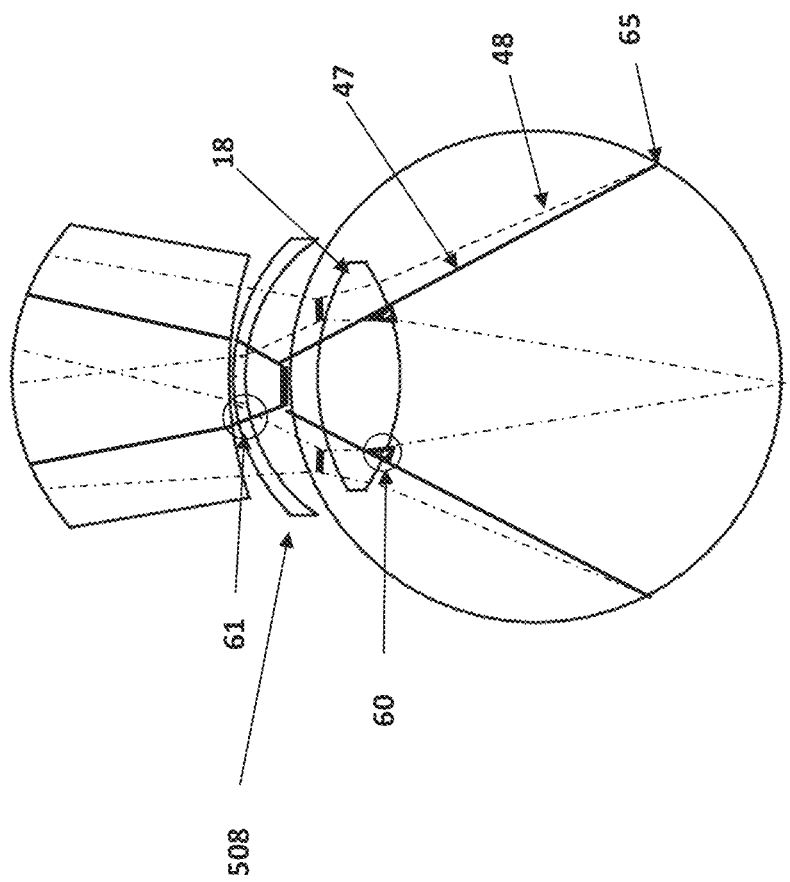
FIG. 7A is an optical schematic illustrating a through the lens imaging system with an extended FOV eye profile view.
Figure 7B:
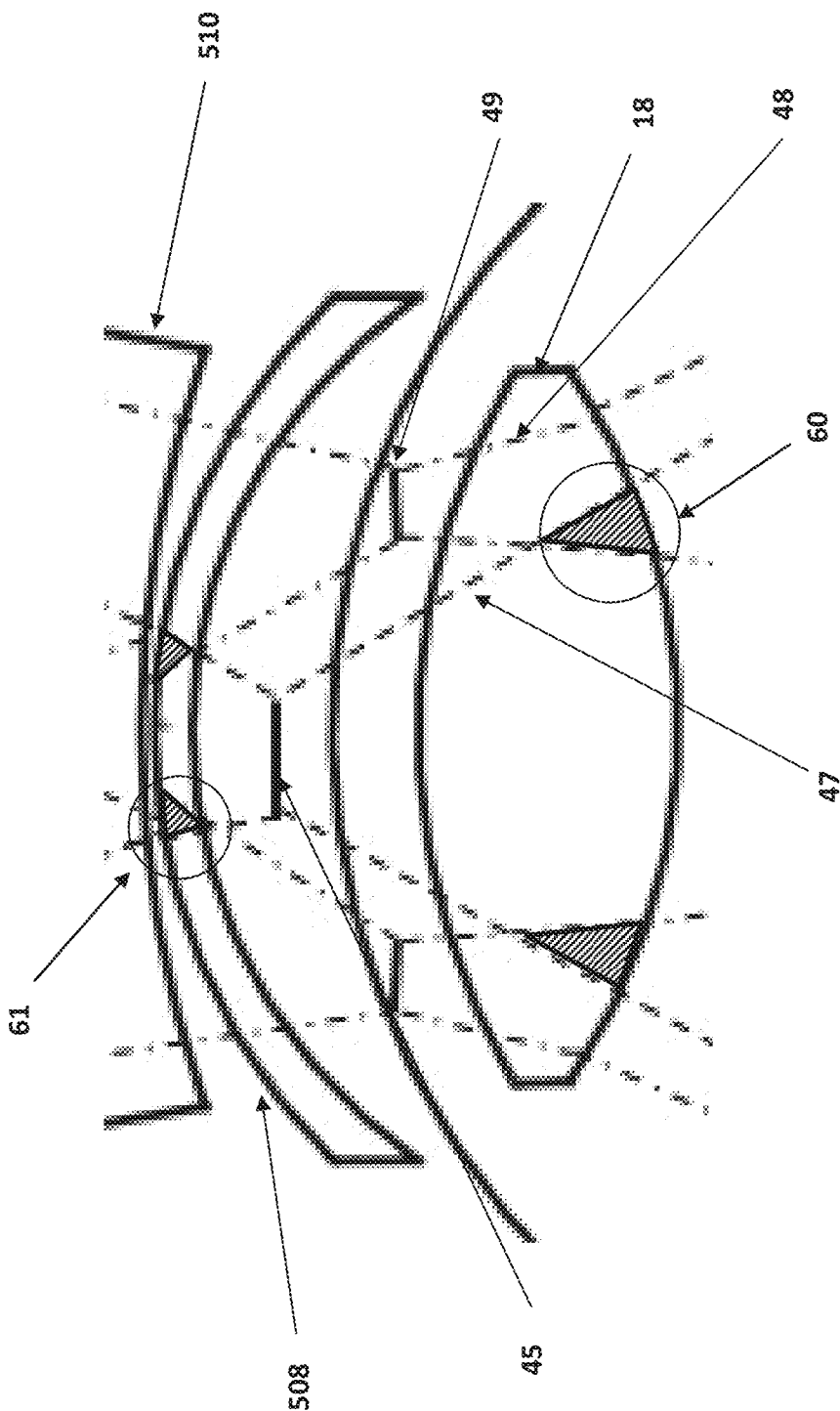
FIG. 7B is an optical schematic illustrating a through the lens imaging system with an extended FOV anterior segment profile view.

However, wider FOVs are sought and attempting to just open up the FOV as shown in FIG. 7A leads to overlap of the incoming and outgoing light, violating the principle of the "cone of silence." Shown in more detail in FIG. 7B there is overlap in the lens 18 in volume 60 and the cornea 508 in volume 61. Likely the periphery of the image will be hazy and frequently retinal cameras have a blue tinged periphery.

Figure 7C:
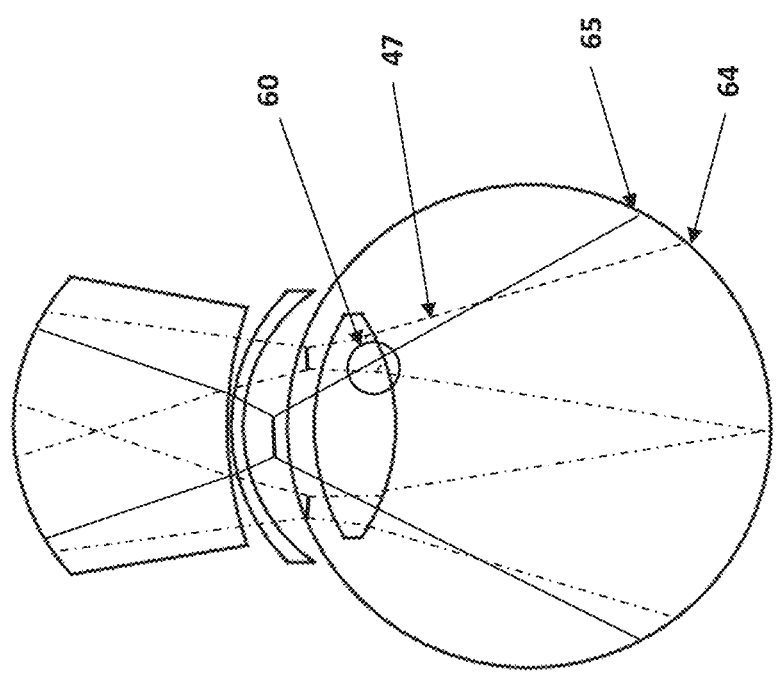
FIG. 7C is an optical schematic illustrating a through the lens imaging system showing extended FOV of imaging but lower FOV of illumination.

FIG. 7C illustrates a cross section of the illumination/imaging system when the FOV is opened to 130 degrees, point 65 on the retina (as illustrated in FIG. 7A) as opposed to 100 degrees, point 64 on the retina. In this instance the illumination field has not been increased and remains at 100 degrees, return rays 47 even though imaging is opened up to 130 degrees.

Figure 7E:
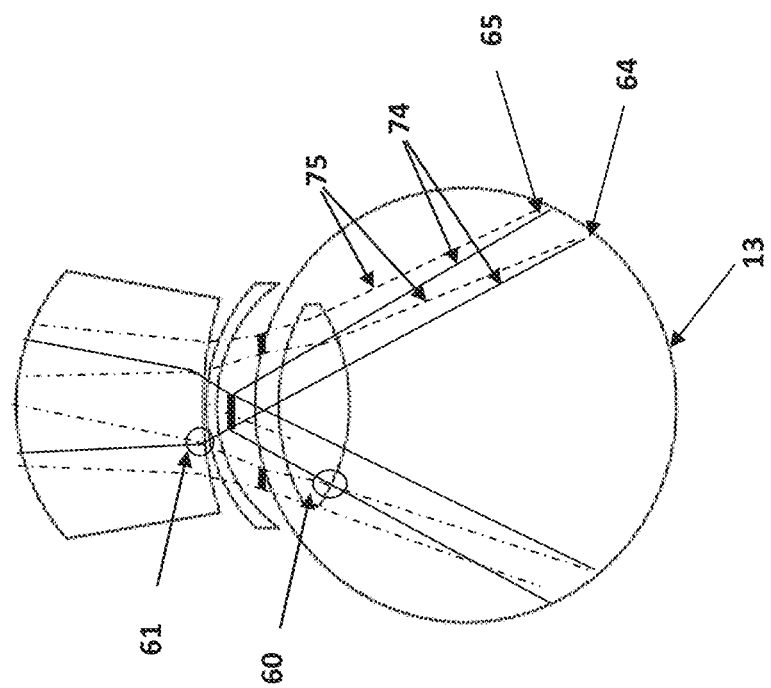
FIG. 7E is an optical schematic illustrating a through the lens imaging system using a ring image of a two image set to avoid the cone of silence.
Figure 7D:
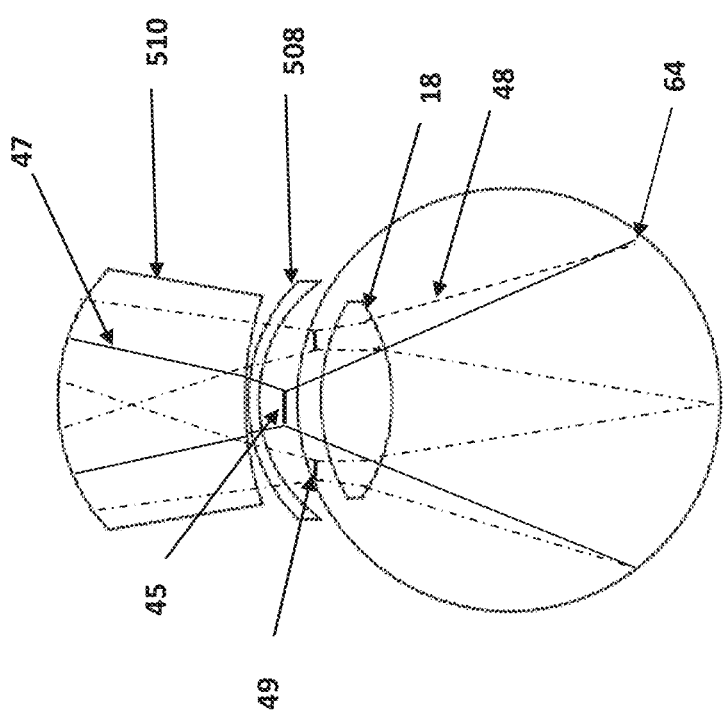
FIG. 7D is an optical schematic illustrating a through the lens imaging system using a central image of a two image set to avoid the cone of silence.

A solution to this violation of the cone of silence is shown in FIGS. 7D and 7E. The system is constructed such that the FOV and field of illumination can be delivered at 130 degrees. Then the system will be set to obtain and merge two images, according to techniques, protocols, and means disclosed below. Referring to FIG. 7D, a first image as obtained that is constricted temporarily to 100 degrees at the sensor and the retina illuminated also to 100 degrees. This produces the same image as the system shown in FIG. 6A. This is accomplished as shown in FIG. 7I by using a spatial light modulator 710 located adjacent or at the image plane 560 and intercepting the light 69 just before the image sensor 562.

Figure 7H:
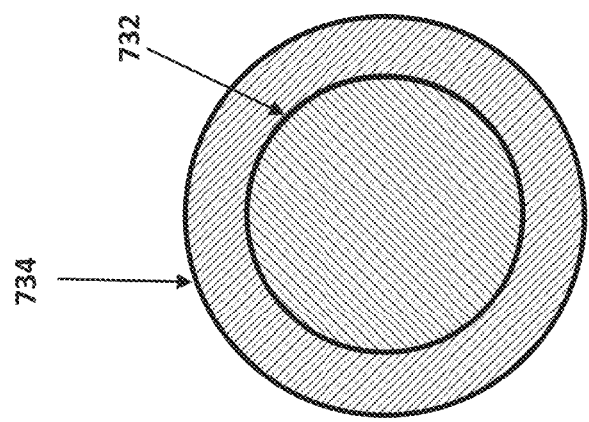
FIG. 7H is a schematic diagram illustrating combination of the central image and the outer ring image according to an embodiment of the present invention.
Figure 7G:
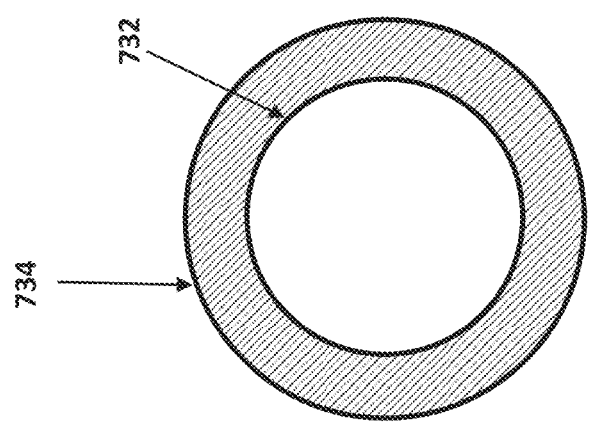
FIG. 7G is a schematic diagram illustrating imaging of an outer ring image according to an embodiment of the present invention.
Figure 7F:
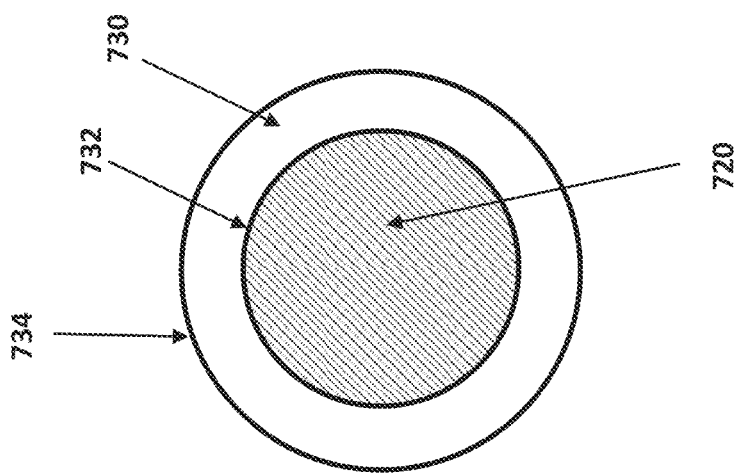
FIG. 7F is a schematic diagram illustrating imaging of a central image according to an embodiment of the present invention.

The CCD shutter is opened and left open during this process so that any and all images will be collected by the array sensor. As shown in FIG. 7F, which is a face on image of the array sensor for the imaging condition illustrated in FIG. 7D, an image of a first central area 720 is formed in the central area, which can be circular. The central area 720 associated with the first central image is characterized by a first field of view, for example, 100 degrees. An outer ring or annular area 730 is not imaged. The outer periphery 734 of the annular area 730 is characterized by a field of view of 130 degrees. The central area 720 and the annular area 730 are contiguous since the periphery of the central area forms a common border with the inner periphery of the annular area. The alignment of the central area and the annular area in the image plane is also present in the object plane on the surface of the retina, providing a first image of a central area of the retina and a second image of an annular area of the retina that surrounds and is contiguous with first image of the central area. One of ordinary skill in the art would recognize many variations, modifications, and alternatives.

Then the spatial light modulator is closed for the central area 720 of the first central image and opened to image the annular area 730, which can also be referred to as an outer ring. Then as shown in FIG. 7E there is illumination provided, system discussed below, in a ring of light 75 on the retina between the first field of view (e.g., 100 degrees) and the field of view of the outer periphery 734 of the annular area 730 (e.g., 130 degrees) and the returning light 74 is also in a ring. Thus, a second image of a portion of the retina is formed as shown in FIGS. 7D and 7G, with the retina illuminated in a ring bounded by rays 75 and the light is received also in a ring bounded by rays 74. Note now that there is no violation of the cone of silence at 60 or at 61 as illustrated in FIG. 7E. Accordingly, both the first image of the central area 720 and the second image of the annular area 730, also referred to as a peripheral area, are free from scatter and the image sensor accumulates both the first image of the central area 720 and the second image of the peripheral area 730 to provide a final combined image as shown in make final image as shown in FIG. 7H. As discussed above, although FIGS. 7F-7H show central and annular areas in the image plane, corresponding areas in the object plane (i.e., the retina) will be present and the discussion associated with the image plane is applicable to the object plane as appropriate.

Other embodiments use a CCD that is equipped to obtain one image, then conduct a rapid frame transfer to external memory, and then acquire a second image. Such a sensor can be used to capture these images and then the external scatter in the first image outside the first field of view (e.g., 100 degrees) could be removed digitally. These sensors are of the interline class and are frequently used for particle image velocimetry (PIV) applications and time between frames can run as low as 80 microseconds.

Third Solution to Scatter/Contrast: Ultra-Wide Field Images

To open up the FOV to 150 degrees, a more complex segmented imaging process can be utilized according to an alternative embodiment. As discussed above, the central image of the central area of the retina (e.g., an image with a field of view of 100 degrees) can be the first imaging step, but the imaging of the annular area of the retina (i.e., outer ring) is characterized by a wider field of view (e.g., an additional 22.5 degrees of width instead of 15 degrees) and a more complex system is employed for imaging of the outer ring.

Figure 8A:
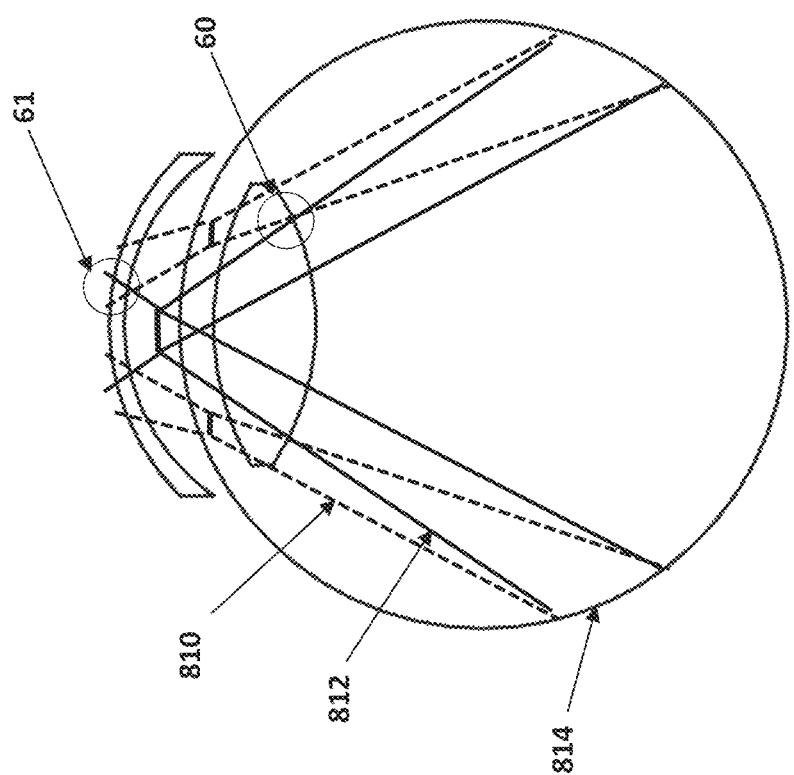
FIG. 8A is an optical schematic illustrating a profile view of illumination and imaging of an outer ring according to an embodiment of the present invention.

FIG. 8A is illustrates a profile view of an eye including illumination and imaging of an outer ring according to an embodiment of the present invention. As discussed above, the first image of the first portion of the retina is obtained at a first field of view (e.g., 100 degrees) and in FIG. 8A, only the outer ring is depicted. The portion 814 of the retina is illuminated in an annular manner, with portion 814 representing a radial line extending across the annulus, enabling imaging of the outer ring. The outer illumination ring bounded by rays 810 now covers the retina with a width of 22.5 degrees on each side of the first (i.e., central) image. As a result, the injected light for the rays 810 on the outer periphery of the outer ring will intersect with the returning light illustrated by rays 812 in volume 61 located at the cornea even though it does not in volume 60 located at the lens of the eye. However, the intersection with incoming and outgoing light in volume 61 at the cornea occurs from the opposite side of the retina.

Figure 8B:
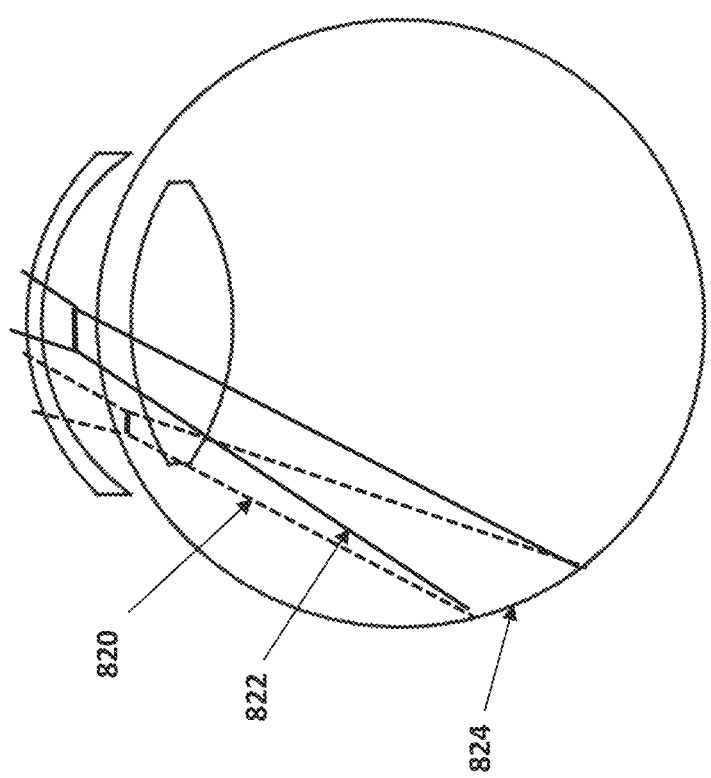
FIG. 8B is an optical schematic illustrating ultra-wide outer ring illumination and imaging using azimuthal segmenting as well as radial segmenting according to an embodiment of the present invention.

FIG. 8B illustrates ultra-wide outer ring illumination and imaging using azimuthal segmenting as well as radial segmenting according to an embodiment of the present invention. As shown in FIG. 8B, by limiting the azimuthal dimension of the ring, the intersection between incoming and outgoing light from across the retina can be avoided.

In the profile view of the eye illustrated in FIG. 8B, illumination and imaging of an outer ring are shown over an azimuthal segment making up a portion of the annular ring. As discussed above, the first image of the first portion of the retina is obtained at a first field of view (e.g., 100 degrees) (i.e., a central image) and in FIG. 8B, only the outer ring is depicted. The outer illumination ring bounded by rays 820 now covers the retina with a width of 22.5 degrees on each side of the first (i.e., central) image. The injected light is represented by rays 820 on the outer periphery of the outer ring and the return light is represented by rays 822. A portion 824 of the retina represents a radial line extending across the azimuthal segment of the annular ring.

Figure 8C:
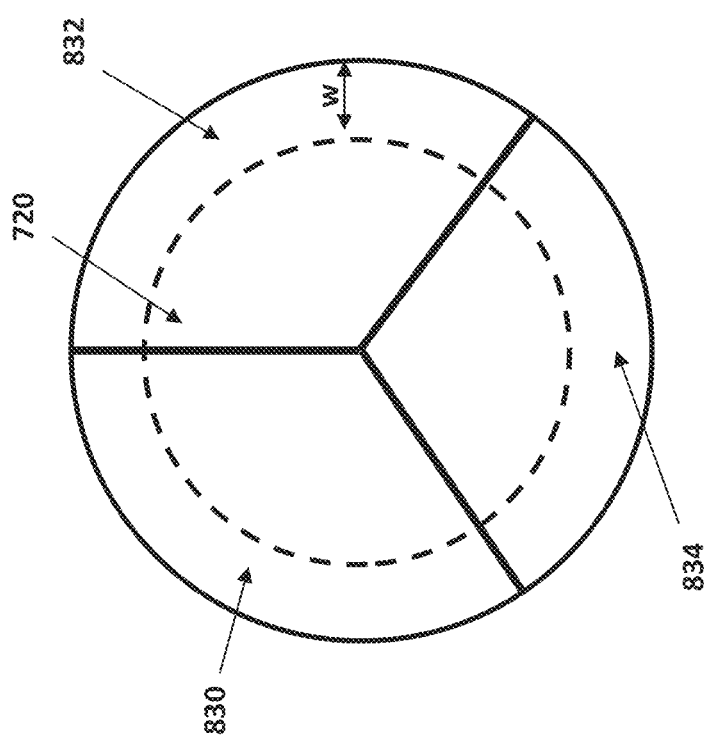
FIG. 8C is a schematic diagram illustrating image segmenting at a sensor according to an embodiment of the present invention.

FIG. 8C illustrates a view from along the optical axis of azimuthal segments according to an embodiment of the present invention. In FIG. 8C, a three quadrant version with azimuthal segments 830, 832, and 834 and central area 720, also referred to as a central segment, is illustrated, with the azimuthal segments being illuminated in sequence and with the appropriate masking in some embodiments. Referring to FIG. 7F, peripheral area 730 has been divided into azimuthal segments and the width of the peripheral area has been increased from 15 degrees to 22.5 degrees, although other widths can be used. The additional field of view width is illustrated by width w in FIG. 8C, for example, 22.5 degrees, although other additional widths can be utilized. The central image of the central segment 720 of the retina is thus obtained and combined with the azimuthal images of the outer ring of the retina (azimuthal segments 830, 832, and 834) to form a combined image of the retina.

Although three quadrants with a first azimuthal range (i.e., 0-120 degrees), a second azimuthal range (120-240 degrees), and a third azimuthal range (i.e., 240-360 degrees) is illustrated in FIG. 8C, the present invention is not limited to this particular implementation. In other implementations, fewer azimuthal ranges are utilized (e.g., two azimuthal ranges) or additional azimuthal ranges are utilized (e.g., four or more azimuthal ranges). Additionally, although the increase in field of view of an additional width of 22.5 degrees is illustrated in FIG. 8C, the present invention is not limited to this particular width and other additional widths are included within the scope of the present invention. One of ordinary skill in the art would recognize many variations, modifications, and alternatives.

As stated above, embodiments of the present invention provide great clinical advantage via the addition of OCT to the hand-held imager and contrast with conventional systems that are heavy, have narrow FOVs, are in general hard to use, and do not have a bright field or fluorescein angiography built in. Some current systems obtain an image in three dimensions over a square, two-dimensional area of the retina and save this data. Then the en face OCT data is displayed in two dimensions (e.g., x and y) with a separate color line over the upper part of this image. This line scans slowly downward while simultaneously displaying the two dimensional OCT data (e.g., x and z). While this gives the clinical data on the layers in the retina, there is a great difficulty in locating the OCT data on the bright field. Thus, to address these shortcomings, embodiments of the present invention present the line indicating the location of the OCT x-z data on the real-time bright field. A plurality of lines can be utilized to provide 3D data. One of ordinary skill in the art would recognize many variations, modifications, and alternatives.

Figure 9A:
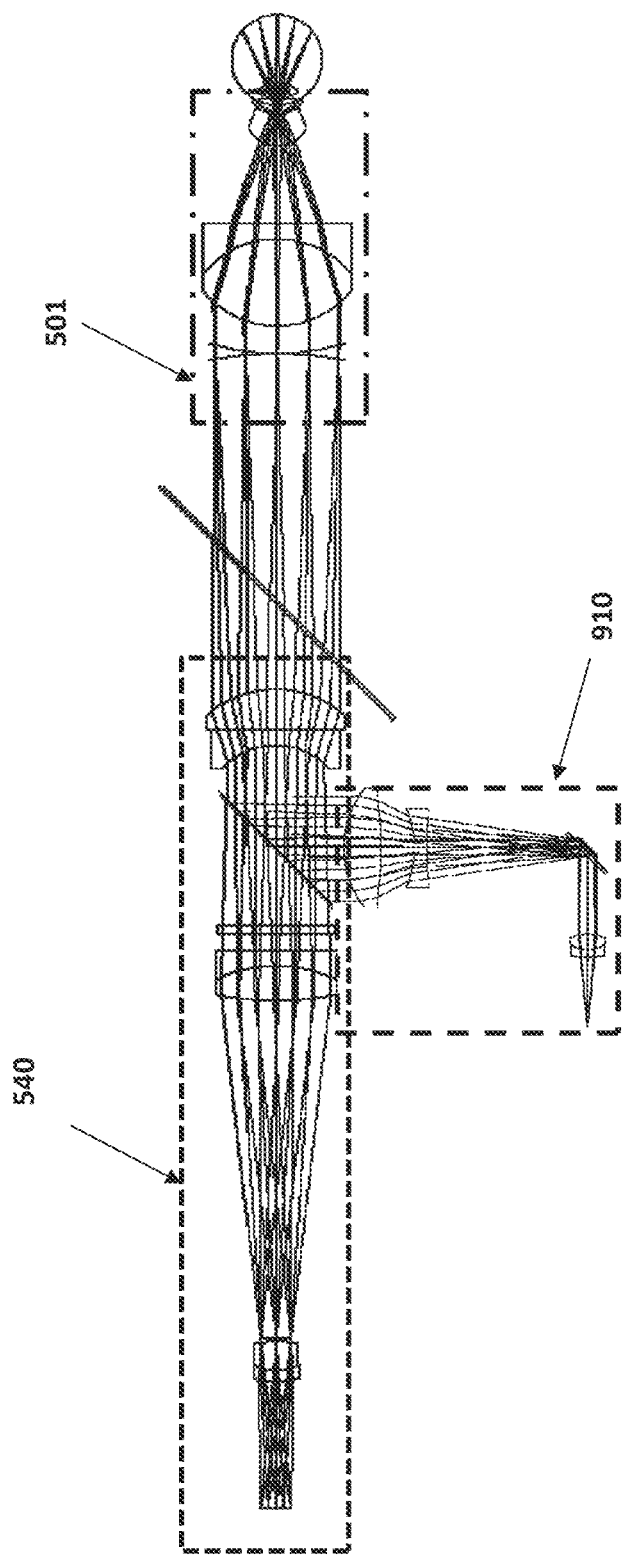
FIG. 9A is an optical schematic illustrating a compact OCT for hand-hand imaging integrated with a hand-held imager according to an embodiment of the present invention.
Figure 9B:
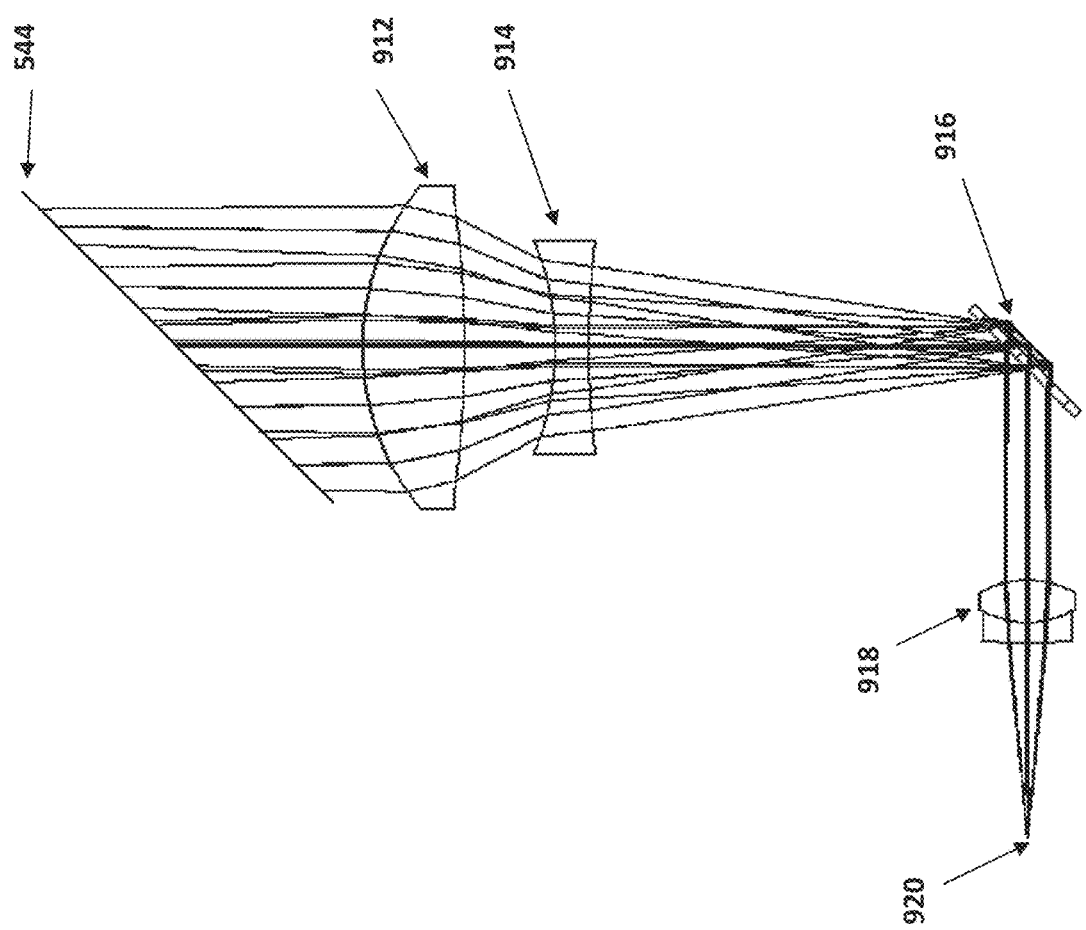
FIG. 9B is an optical schematic illustrating details of an OCT beam train according to an embodiment of the present invention.

FIG. 9A is a schematic diagram illustrating a hand held imager with integrated OCT according to an embodiment of the present invention. Referring to FIG. 9A, the OCT optical chain is illustrated that would be utilized in imaging a retina. Imaging lens group 540 is the segment of the system at the rear portion of the imaging system, portions of which were described in relation to FIG. 5C. The objective lens set 501 is illustrated as well and the optional OCT return/transmit segment 910. In FIG. 9B, details of the OCT imaging/transmit section 910 are illustrated. There is an image at focal point 920 and a single fiber transmitting/receiving the OCT light to and from the OCT engine. Lens 918 projects the IR light forward and there is a pupil 916 at MEMS mirror 917. Lens 914 and lens 912 project the IR light towards beam splitter 544, which reflects the IR light into the optical system of the camera.

In an embodiment, the software that is used to send the x and y signals to the MEMS mirror 917 also provides data to the display for adding an indication line to the bright field data. It will be appreciated that aberration correction, both at visible and IR wavelengths is provided such that the OCT image resolution requirements are met by the rear optics in FIG. 9A.

Figure 9C:
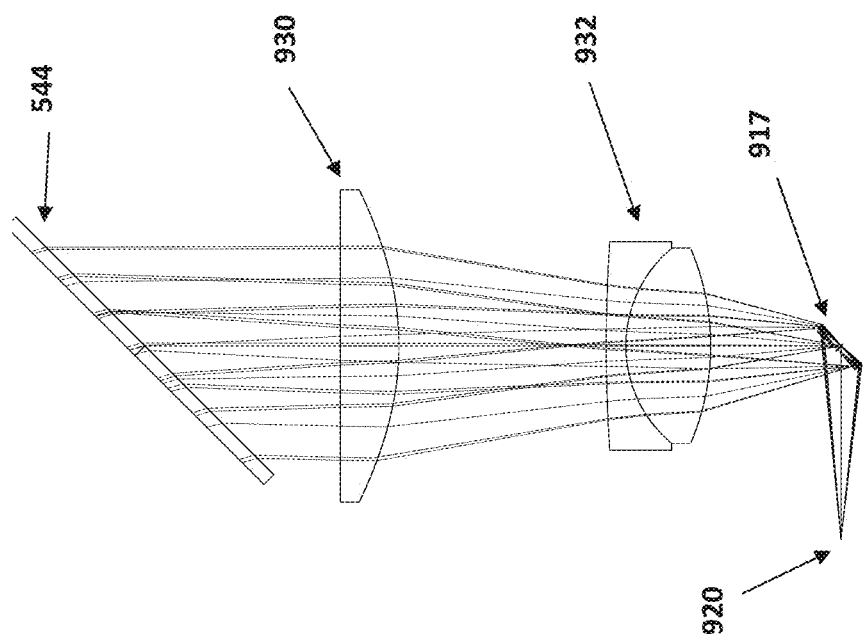
FIG. 9C is an optical schematic illustrating details of an OCT beam train according to another embodiment of the present invention.

FIG. 9C is an optical schematic illustrating details of an OCT beam train according to another embodiment of the present invention. The system illustrated in FIG. 9C shares common elements with the system illustrated in FIG. 9B and the description related to FIG. 9B is applicable to the system illustrated in FIG. 9C as appropriate. In the OCT system illustrated in FIG. 9C, there is an image at focal point 920 and a single fiber transmitting/receiving the OCT light to and from the OCT engine. IR light is projected toward MEMS mirror 917. Lens 932 and lens 930 project the IR light towards beam splitter 544, which reflects the IR light into the optical system of the camera.

FIG. 10 is a simplified schematic diagram illustrating a hand-held imager for imaging the retina of an eye according to an embodiment of the present invention. The hand-held imager 1000 includes a housing 1002 that encloses one or more of the optical elements described herein. Referring to FIG. 10, the hand-held imager 1000 is placed adjacent the eye 1010 that is to be imaged. The objective lens set 501, includes optical elements including the objective lens 510 and the second lens 512 illustrated in FIG. 5A. The illuminator 1020, also referred to as an illumination source, provides the illumination light 505 illustrated in FIG. 5A. The beam splitter 520, directs the illumination light 505 toward the objective lens set 501.

Light reflected from the eye passes through the objective lens set 501 in the return path, passes through beam splitter 522 and is imaged using the imaging lens set 540 to form an image at image plane 560 associated with the image sensor 562. An optional OCT return/transmit segment 910, can be mounted on an outer surface of housing 1002 in some embodiments. In other embodiments, the OCT segment can be disposed in the housing along with other optical elements and segments. A grip 1040 is provided surrounding the objective lens set 501 to enable a user to hold the hand-held imager in their hand. Typically, the length of the grip is on the order of 6 inches to facilitate holding of the hand-held imager by medical personnel.

In some embodiments, the illuminator or illumination source 1020, the objective lens set 501, and the imaging lens set 540 are disposed inside the housing, providing a compact package suitable for hand-held use. Power and communications are provided to the hand-held unit through power/communications cable 1050, which can be connected to the housing at input/output connector 1052.

According to an embodiment of the present invention, a hand-held imager for imaging a retina of the eye is provided. The hand-held imager includes a housing. A number of optical elements are disposed in the housing including an illumination source operable to generate illumination light and a beam splitter operable to receive the illumination light and direct the illumination light along an optical axis. An objective lens set is disposed along the optical axis and includes a field lens disposed along the optical axis and an objective lens disposed along the optical axis and operable to contact a cornea of the eye. An aerial image is formed adjacent to the field lens. Also disposed in the housing are an an image sensor and one or more lenses disposed along the optical axis between the beam splitter and the image sensor. The one or more lenses are operable to form a sensor image at the image sensor.

In one use case, the hand-held imager is held in the hand of a user for use during retinal imaging. In another use case, the patient's head is supported in a chin-forehead rest and the hand-held imager is mounted adjacent the chin-forehead rest. Thus, the use of the term hand-held is not intended to limit the scope of the present invention to only being held in a user's hand, but to include applications in which the retinal imager is mounted. One of ordinary skill in the art would recognize many variations, modifications, and alternatives.

Figure 11:
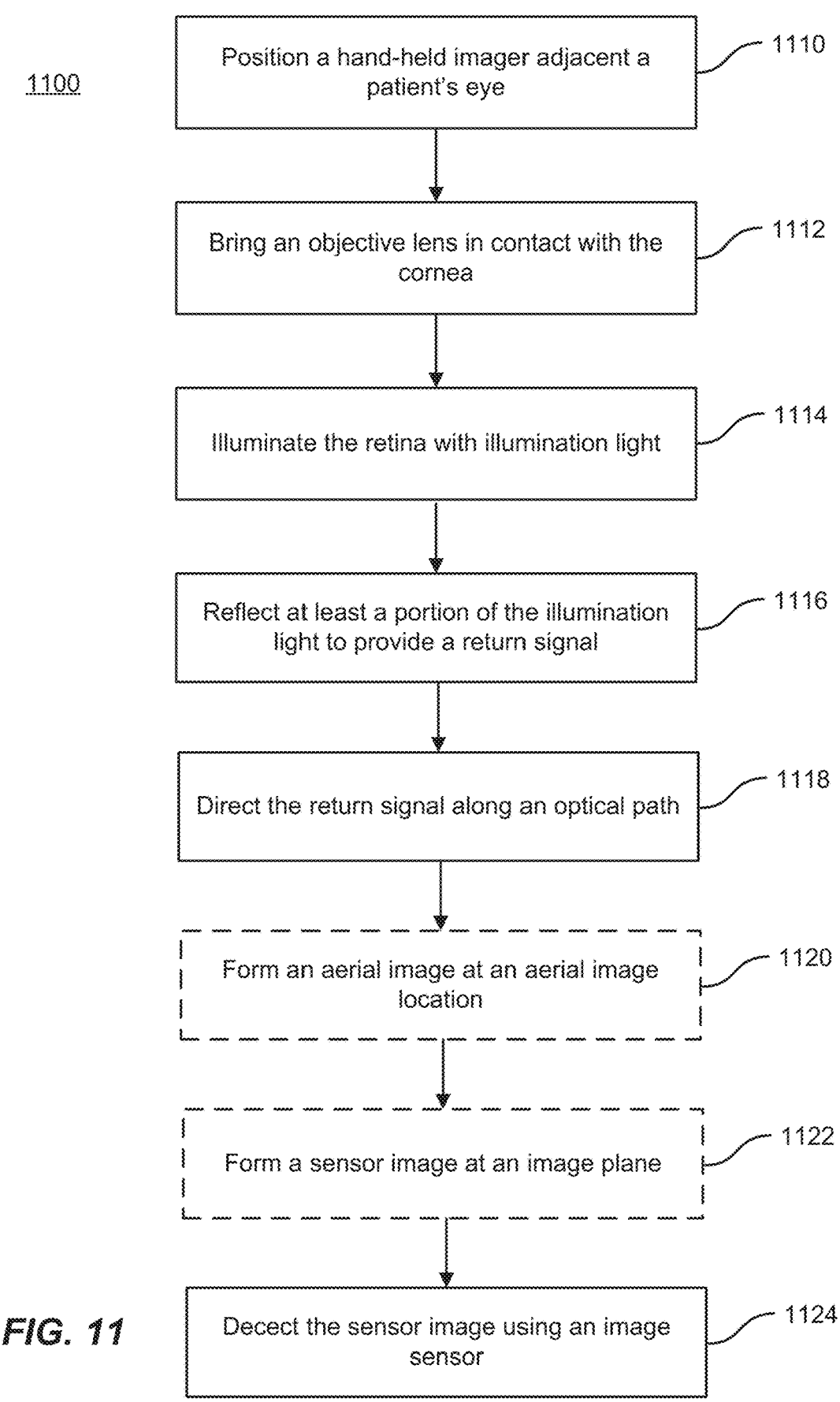
FIG. 11 is a simplified flowchart illustrating a method of operating a hand-held imager to image a retina of an eye of a patient according to an embodiment of the present invention.

FIG. 11 is a simplified flowchart illustrating a method of operating a hand-held imager to image a retina of an eye of a patient according to an embodiment of the present invention. The method 1100 includes positioning the hand-held imager adjacent the eye of the patient (1110). The hand-held imager includes an illumination source operable to generate illumination light and an objective lens set including an objective lens and a second lens. The objective lens can be implemented as a single element objective lens in some embodiments. In some embodiments, the second lens serves as a field lens. The method also includes bringing the objective lens in contact with a cornea of the eye (1112) and illuminating the retina of the eye with the illumination light passing through the objective lens set (1114).

The method further includes reflecting at least a portion of the illumination light off of the retina to provide a return signal (1116), directing the return signal along an optical path, (1118), and detecting a sensor image at the image plane using an image sensor (1124).

In some embodiments, the method also includes forming an aerial image along the optical path at an aerial image location adjacent to the field lens (1120) and forming the sensor image at an image plane by imaging the aerial image (1122). In these embodiments, the aerial image is characterized by a first image quality and the sensor image at the image plane is characterized by a second image quality higher than the first image quality. As an example, the aerial image can be characterized by chromatic aberration that is not present or is present at a lower level in the sensor image. Merely by way of example, the aerial image can include a tangential image and a sagittal image that have millimeters or more of curvature at the edge and in different directions.

It should be appreciated that the specific steps illustrated in FIG. 11 provide a particular method of operating a hand-held imager to image a retina of an eye of a patient according to an embodiment of the present invention. Other sequences of steps may also be performed according to alternative embodiments. For example, alternative embodiments of the present invention may perform the steps outlined above in a different order. Moreover, the individual steps illustrated in FIG. 11 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 12:
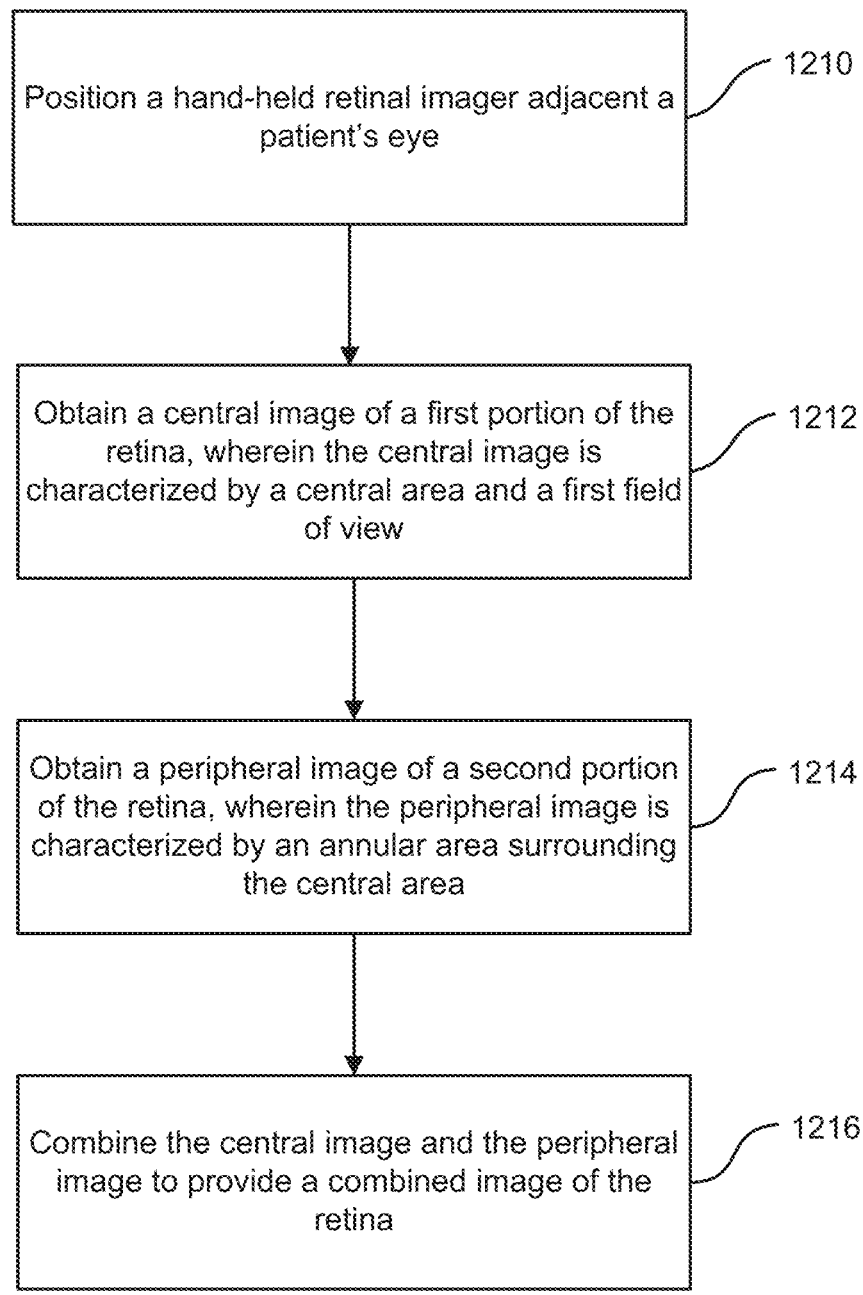
FIG. 12 is a simplified flowchart illustrating a method of imaging a retina of an eye of a patient according to an embodiment of the present invention.

FIG. 12 is a simplified flowchart illustrating a method of imaging a retina of an eye of a patient according to an embodiment of the present invention. The method 1200 includes positioning a hand-held retinal imager adjacent the eye of the patient (1210) and obtaining a first image of a first portion of the retina (1212). The first image is associated with a central area (e.g., a circular area) and a first field of view (e.g., 100 degrees). The first image can be formed on the image plane of the image sensor as illustrated in FIG. 7F.

The method also includes obtaining a second image of a second portion of the retina (1214). The second image is associated with an annular area surrounding the central area. The outer periphery of the annular area is characterized by a second field of view (e.g., 130 degrees) greater than the first field of view. In some embodiments, the first portion of the retina and the second portion of the retina are contiguous. The method further includes combining the first image of the first portion of the retina and the second image of the second portion of the retina to provide a combined image of the retina (1216). Utilizing embodiments of the present invention, the combined image provides higher quality than available if a single image was obtained.

In some embodiments, the hand-held imager includes an illumination source operable to generate illumination light and an objective lens set including an objective lens and a second lens. In an embodiment, obtaining the first image of the first portion of the retina includes bringing the objective lens in contact with a cornea of the eye, illuminating the first portion of the retina with illumination light passing through the objective lens set, and reflecting at least a portion of the illumination light off of the first portion of the retina to provide a return signal. In some embodiments, the peripheral portion of the retina surrounding the central portion is masked off such that it is not illuminated while the first image is obtained. Obtaining the first image can further include directing the return signal along an optical path and detecting a sensor image at the image plane using an image sensor.

In another embodiment, obtaining the second image of the second portion of the retina includes bringing the objective lens in contact with a cornea of the eye, illuminating the second portion of the retina with illumination light passing through the objective lens set, and reflecting at least a portion of the illumination light off of the second portion of the retina to provide a return signal. In some embodiments, the central portion of the retina inside the peripheral portion is masked off such that it is not illuminated while the second image is obtained. Obtaining the second image can further include directing the return signal along an optical path and detecting a sensor image at the image plane using an image sensor.

As described herein, obtaining the first image of the first portion of the retina can include operating a spatial light modulator to illuminate the central area and block light propagating in the annular area surrounding the central area. Obtaining the second image of the second portion of the retina can include operating the spatial light modulator to illuminate the annular area surrounding the central area and block light propagating in the central area. The spatial light modulator can be located adjacent an image plane of an image sensor.

It should be appreciated that the specific steps illustrated in FIG. 12 provide a particular method of imaging a retina of an eye of a patient according to an embodiment of the present invention. Other sequences of steps may also be performed according to alternative embodiments. For example, alternative embodiments of the present invention may perform the steps outlined above in a different order. Moreover, the individual steps illustrated in FIG. 12 may include multiple sub-steps that may be performed in various sequences as appropriate to the individual step. Furthermore, additional steps may be added or removed depending on the particular applications. One of ordinary skill in the art would recognize many variations, modifications, and alternatives.

Figure 13:
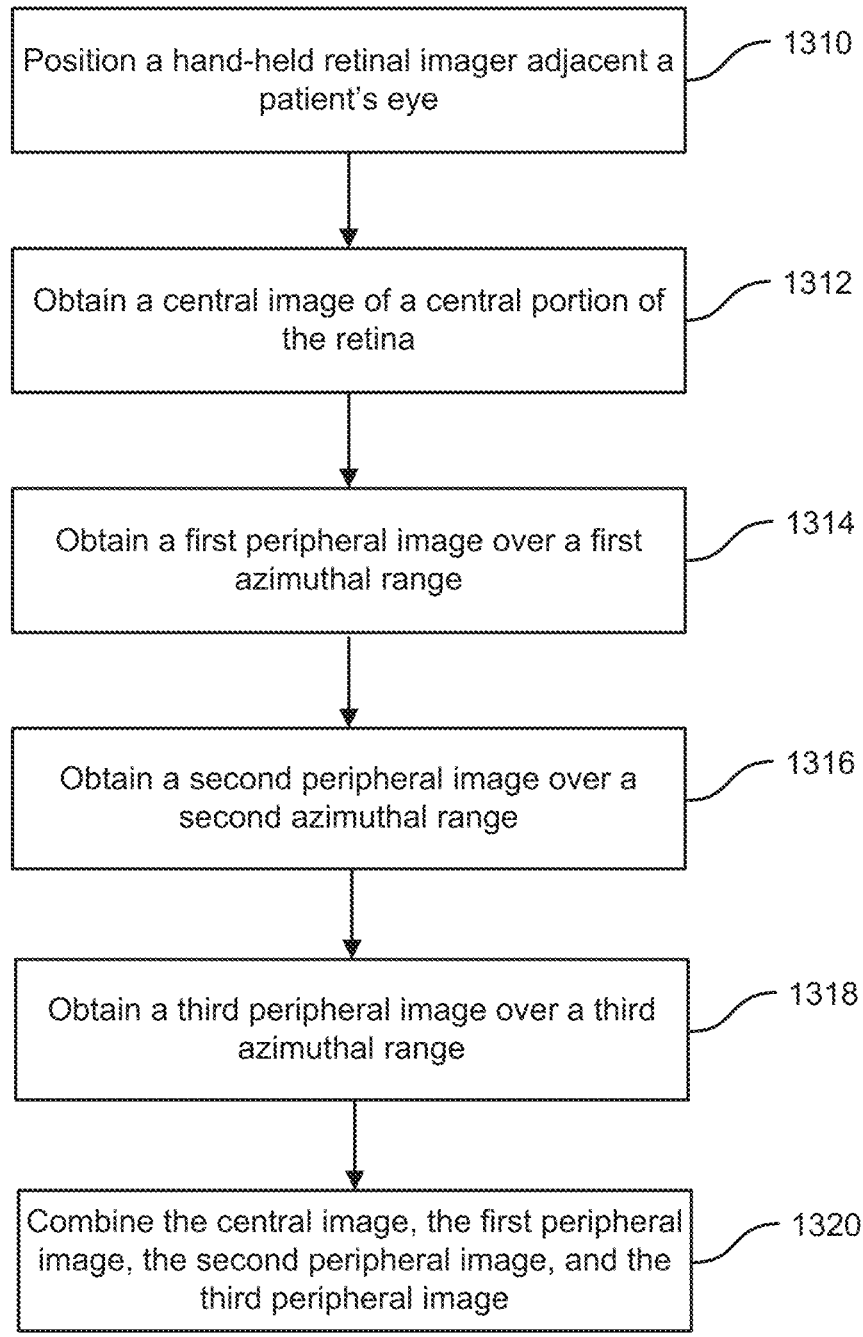
FIG. 13 is a simplified flowchart illustrating a method of forming a wide field of view image of a retina of an eye of a patient according to an embodiment of the present invention.

FIG. 13 is a simplified flowchart illustrating a method of forming a wide field of view image of a retina of an eye of a patient according to an embodiment of the present invention. The method 1300 includes positioning a hand-held retinal imager adjacent the eye of the patient (1310) and obtaining a first image of a first portion (e.g., a central portion) of the retina. The hand-held imager can include an illumination source operable to generate illumination light and an objective lens set including an objective lens and a second lens. The first image is associated with a central area (e.g., a circular area) and a first field of view (e.g., 100 degrees).

In an embodiment, obtaining the first image of the first portion of the retina includes bringing the objective lens in contact with a cornea of the eye and illuminating the first portion of the retina of the eye with the illumination light passing through the objective lens set. Obtaining the first image can also include reflecting at least a portion of the illumination light off of the first portion of the retina to provide a return signal, directing the return signal along an optical path, and detecting a central sensor image at the image plane using an image sensor.

The method also includes obtaining a first additional image of a first additional portion of the retina (1314). The first additional image associated with a first azimuthal range covering a first portion of an annular area surrounding the central area. An outer periphery of the annular area is characterized by a second field of view (e.g., 150 degrees) greater than the first field of view. The method further includes obtaining a second additional image of a second additional portion of the retina (1316). The second additional image is associated with a second azimuthal range covering a second portion of the annular area surrounding the central area. Additionally, The method includes obtaining a third additional image of a third additional portion of the retina (1318). The third additional image is associated with a third azimuthal range covering a third portion of the annular area surrounding the central area. In some embodiments, together, the first azimuthal range, the second azimuthal range, and the third azimuthal range cover a 360 degree range.

In an embodiment, obtaining the first, second, and third additional images of the first, second, and third additional portions of the retina includes bringing the objective lens in contact with a cornea of the eye and sequentially illuminating the first, second, and third additional portions of the retina of the eye with the illumination light passing through the objective lens set. Obtaining the first, second, and third additional images can also include reflecting at least a portion of the illumination light off of the first, second, and third additional portions of the retina to provide first, second, and third return signals, directing the first, second, and third return signals along an optical path, and detecting first, second, and third peripheral sensor images at the image plane using an image sensor.

As an example, obtaining the first image of the first portion of the retina can include operating a spatial light modulator to illuminate the central area and block light propagating in the annular area surrounding the central area. The spatial light modulator can be located adjacent the image plane of the image sensor. Obtaining the first additional image of the first additional portion of the retina can include operating the spatial light modulator to illuminate the first azimuthal range covering the first portion of the annular area surrounding the central area and block light propagating in the central area, in the second azimuthal range covering the second portion of the annular area surrounding the central area, and in the third azimuthal range covering the third portion of the annular area surrounding the central area.

Obtaining the second additional image of the second additional portion of the retina can include operating the spatial light modulator to illuminate the second azimuthal range covering the second portion of the annular area surrounding the central area and block light propagating in the central area, in the first azimuthal range covering the first portion of the annular area surrounding the central area, and in the third azimuthal range covering the third portion of the annular area surrounding the central area. Obtaining the third additional image of the third additional portion of the retina can include operating the spatial light modulator to illuminate the third azimuthal range covering the third portion of the annular area surrounding the central area and block light propagating in the central area, in the first azimuthal range covering the first portion of the annular area surrounding the central area, and in the second azimuthal range covering the second portion of the annular area surrounding the central area.

The method also includes combining the first image of the first portion of the retina, the first additional image of the first additional portion of the retina, the second additional image of the second additional portion of the retina, and the third additional image of the third additional portion of the retina to provide a combined image of the retina (1320).

As illustrated in FIG. 8C, the first portion of the retina can be contiguous with the first portion of the annular area surrounding the central area, the second portion of the annular area surrounding the central area, and the third portion of the annular area surrounding the central area. Additionally, the first portion of the annular area surrounding the central area can be contiguous with the second portion of the annular area surrounding the central area, the second portion of the annular area surrounding the central area can be contiguous with the third portion of the annular area surrounding the central area, and the third portion of the annular area surrounding the central area can be contiguous with the first portion of the annular area surrounding the central area.

It should be appreciated that the specific steps illustrated in FIG. 13 provide a particular method of forming a wide field of view image of a retina of an eye of a patient according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications. One of ordinary skill in the art would recognize many variations, modifications, and alternatives.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A retinal imager for imaging a retina of an eye, the retinal imager comprising:
   a housing containing an optical system comprising:
   an illumination source operable to generate illumination light;
   a beam splitter operable to receive the illumination light and direct the illumination light along an optical axis;
   a field lens disposed along the optical axis;
   an image sensor;
   an objective lens disposed along the optical axis and operable to contact a cornea of the eye, wherein the objective lens is operable to inject the illumination light into the eye as an illumination ring; and
   an imaging lens group disposed along the optical axis between the beam splitter and the image sensor, wherein the imaging lens group is operable to form a sensor image at the image sensor and wherein an entrance pupil and the illumination ring are located at different positions along the optical axis.

2. The retinal imager of claim 1, wherein the illumination source is disposed inside the housing.

3. The retinal imager of claim 1, wherein the imaging lens group is disposed inside the housing.

4. The retinal imager of claim 1, wherein the objective lens is mounted at a periphery of the housing.

5. The retinal imager of claim 1, wherein the housing includes a grip operable to be held by a hand of a user.

6. The retinal imager of claim 1, wherein a second beam splitter is operable to be positioned within the imaging lens group.

7. The retinal imager of claim 6, wherein an optical coherence tomography (OCT) beam train is optically coupled to the second beam splitter.

8. The retinal imager of claim 7, wherein the OCT beam train is mounted on an outer surface of the housing.

9. The retinal imager of claim 7, wherein OCT beam train is disposed inside the housing.

10. The retinal imager of claim 7, wherein the OCT beam train comprises a micro-electromechanical system (MEMS) mirror, and where a pupil is formed on the MEMS mirror.

11. The retinal imager of claim 7, wherein a single fiber is utilized to transmit and receive light propagating along the OCT beam train.

12. The retinal imager of claim 1, wherein the housing further comprises an input/output (I/O) connection.

13. The retinal imager of claim 12, wherein the I/O connection is coupled to a communications cable being operable to communicate power and communications with optical elements disposed within the housing.

14. The retinal imager of claim 1, wherein an aerial image is formed adjacent to the field lens.

15. The retinal imager of claim 14, wherein the aerial image comprises an object for the sensor image at the image sensor.

16. The retinal imager of claim 14, wherein the aerial image is formed between the field lens and the beam splitter, and wherein the objective lens is further operable to receive reflected light from a retina and the aerial image is formed by the reflected light.

17. The retinal imager of claim 1, wherein the objective lens comprises a single element objective lens, and wherein the illumination light is injected into the eye through the single element objective lens.

18. The retinal imager of claim 1, wherein the sensor image comprises a central area, wherein the central area us circular, and wherein the sensor image further comprises an annular area surrounding the central area.

19. The retinal imager of claim 18, wherein a periphery of the central area forms a common border with an inner periphery of the annular area.

20. The retinal imager of claim 18, wherein the sensor image further comprises three azimuthal segments.

* * * * *